(12) United States Patent
Fan et al.

(10) Patent No.: US 11,220,489 B2
(45) Date of Patent: Jan. 11, 2022

(54) PROCESS FOR PREPARING INDOLE CARBOXAMIDE COMPOUNDS

(71) Applicant: BRISTOL-MYERS SQUIBB COMPANY, Princeton, NJ (US)

(72) Inventors: Junying Fan, Monmouth Junction, NJ (US); Peng Geng, Hillsborough, NJ (US); Neil A. Strotman, Flemington, NJ (US); Alina Borovika, Brooklyn, NY (US); Jason Michael Stevens, Cranford, NJ (US); Dimitri Skliar, Staten Island, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 492 days.

(21) Appl. No.: 16/328,447

(22) PCT Filed: Aug. 31, 2017

(86) PCT No.: PCT/US2017/049589
§ 371 (c)(1),
(2) Date: Feb. 26, 2019

(87) PCT Pub. No.: WO2018/045157
PCT Pub. Date: Mar. 8, 2018

(65) Prior Publication Data
US 2021/0276970 A1    Sep. 9, 2021

Related U.S. Application Data

(60) Provisional application No. 62/382,938, filed on Sep. 2, 2016.

(51) Int. Cl.
*C07D 401/04*    (2006.01)
(52) U.S. Cl.
CPC ................. *C07D 401/04* (2013.01)
(58) Field of Classification Search
CPC .................................................. C07D 401/04
See application file for complete search history.

(56) References Cited

U.S. PATENT DOCUMENTS 9,688,629 B2 * 6/2017 Liu ...................... C07D 413/04

FOREIGN PATENT DOCUMENTS

WO    2005082865 A1    9/2005
WO    WO2016065226 A1    4/2016

OTHER PUBLICATIONS

Cabello-Sanchez et al., "Palladium-Mediated N-Arylation of Heterocyclic Diamines: Insights into the Origin of an Unusual Chemoselectivity", J. Org. Chemistry, vol. 72, pp. 2030-2039 (2007).

(Continued)

*Primary Examiner* — D Margaret M Seaman
(74) *Attorney, Agent, or Firm* — Gary Greenblatt

(57) ABSTRACT

Disclosed is a process for preparing (S)-4-(3-(but-2-ynamido)piperidin fluoro-2,3-dimethyl-1H-indole-7-carboxamide, comprising the steps of: preparing a compound of Formula (III); converting the compound of Formula (III) to a compound of Formula (V); and reacting the compound of Formula (V) with a compound of Formula (VI) to provide (S)-4-(3-(but-2-ynamido)piperidin-1-yl)-5-fluoro-2,3-dimethyl-1H-indole-7-carboxamide.

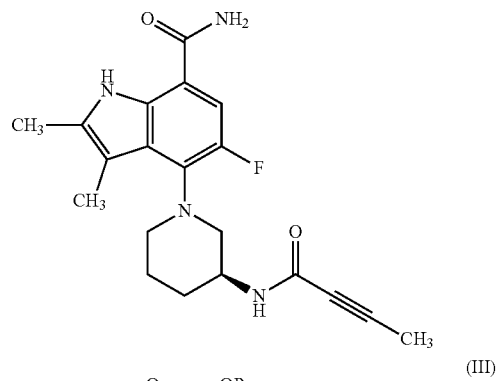

(III)

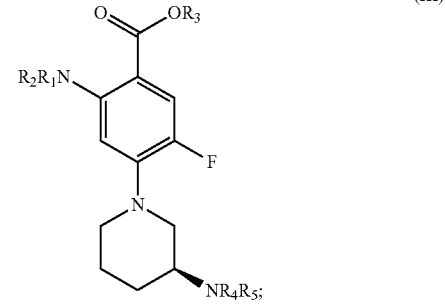

(V)

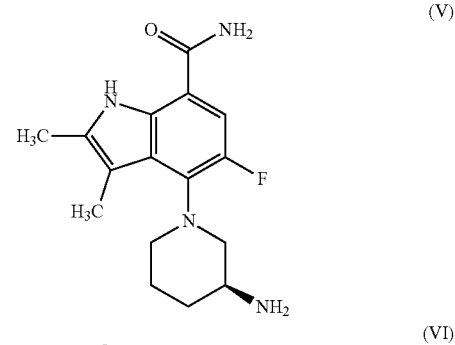

(VI)

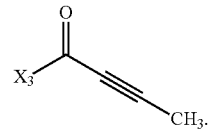

20 Claims, No Drawings

(56) References Cited

OTHER PUBLICATIONS

International Preliminary Report on Patentability PCT/US2017/049589, dated Mar. 5, 2019.
Jean et al., "Palladium-Mediated Arylation of 3-Aminopiperidines and 3-Aminopyrrolidines", J. Org. Chemistry, vol. 69, pp. 8893-8902 (2004).
Roth, et al., Synthese von Indol-un Carbazol-Derivaten aus α-Hydroxyketonen und aromatischen Aminen, Archiv der Pharmazie, 1972, Heft 3, 13 pgs.

* cited by examiner

PROCESS FOR PREPARING INDOLE CARBOXAMIDE COMPOUNDS

CROSS-REFERENCE TO RELATED APPLICATIONS

This application is a national phase application under 35 U.S.C. § 371 of International Patent Application No. PCT/US2017/049589, filed Aug. 31, 2017, which claims priority to U.S. Application Ser. No. 62/382,938, filed Sep. 2, 2016, which are expressly incorporated fully herein by reference.

DESCRIPTION

The present invention generally relates to a process for preparing indole carboxamide compounds.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause dysregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

WO 2016/065226 discloses indole carboxamide compounds useful as Btk inhibitors, including (S)-4-(3-(but-2-ynamido)piperidin-1-yl)-5-fluoro-2,3-dimethyl-1H-indole-7-carboxamide (Example 223), which has the structure:

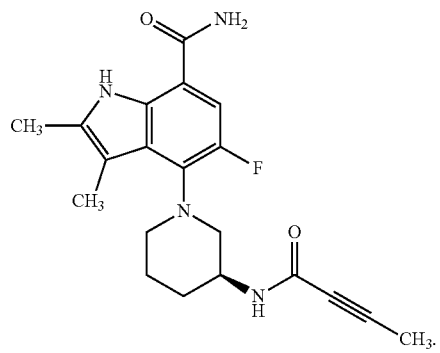 [SMILES: CC#CC(=O)N[C@H]1CCCN(c2c(F)cc(C(N)=O)c3[nH]c(C)c(C)c23)C1]

Also disclosed is multistep synthesis process for preparing (S)-4-(3-(but-2-ynamido) piperidin-1-yl)-5-fluoro-2,3-dimethyl-1H-indole-7-carboxamide.

There are difficulties associated with the adaptation of the multistep synthesis disclosed in WO 2016/065226 to larger scale synthesis, such as production in a pilot plant or a manufacturing plant for commercial production. Further, there is a continuing need to find a process that has few synthesis steps, provides higher yields, and/or generates less waste.

Applicants have discovered a new synthesis process for the preparation of (S)-4-(3-(but-2-ynamido)piperidin-1-yl)-5-fluoro-2,3-dimethyl-1H-indole-7-carboxamide that has fewer synthesis steps and/or provides higher yields than the process disclosed in WO 2016/065226. Furthermore, this process contains no metal-catalyzed steps, no genotoxic intermediates, and is adaptable to large scale manufacturing.

SUMMARY OF THE INVENTION

The present invention provides a process making (S)-4-(3-(but-2-ynamido) piperidin-1-yl)-5-fluoro-2,3-dimethyl-1H-indole-7-carboxamide.

The present invention also provides intermediates and process for preparing intermediates useful in the process of preparing (S)-4-(3-(but-2-ynamido)piperidin-1-yl)-5-fluoro-2,3-dimethyl-1H-indole-7-carboxamide.

DETAILED DESCRIPTION

The first aspect of the invention provides a process for preparing a compound of Formula (V):

(V)

[Structure of Formula (V): indole with carboxamide, 2,3-dimethyl, 4-(3-aminopiperidin-1-yl), 5-fluoro substituents]

comprising the steps of:
(a) reacting a compound of Formula (I) and a compound of Formula (II):

(I)

[Structure of Formula (I)]

(II)

[Structure of Formula (II)]

to provide a compound of Formula (III):

(III)

[Structure of Formula (III)]

and
(b) converting said compound of Formula (III) to said compound of Formula (V) by steps (b1), (b2), and (b3), in any order:
  (b1) forming an indole group by reaction with a compound of Formula (IVa) or a compound of Formula (IVb):

(IVa)

[Structure of Formula (IVa)]

(IVb)

[Structure of Formula (IVb)]

(b2) converting said —$NR_4R_5$ group to —$NH_2$; and
  (b3) converting said —$OR_3$ group to —$NH_2$;
wherein:
$X_1$ is halo, —$NO_2$, —$OS(O)_2R$, or —$N_2^+$;
$X_2$ is Cl, Br, I, —OH, —$OS(O)_2R$, acyloxy, or trialkylsiloxy;
$R_1$ and $R_2$ are independently selected from H, benzyl, substituted benzyl, 4-methoxyphenyl, acyl, —$S(O)_2Ar$, tert-butoxycarbonyl, or benzyloxycarbonyl;
$R_3$ is H, $C_{1-8}$ alkyl, aryl, or heteroaryl;
$R_4$ and $R_5$ are independently selected from H, benzyl, 4-methoxybenzyl, 4-methoxyphenyl, acyl, —$S(O)_2R$, tert-butoxycarbonyl, or benzyloxycarbonyl;
$R_8$ is H, $C_{1-3}$ alkyl, or aryl; and
each R is independently $C_{1-3}$ alkyl or aryl.

The second aspect of the invention provides a process for preparing a compound of Formula (VII), comprising the steps of:

(VII)

[Structure of Formula (VII)]

(a) reacting a compound of Formula (I) and a compound of Formula (II):

(I)

[Structure of Formula (I)]

(II)

[Structure of Formula (II)]

to provide a compound of Formula (III):

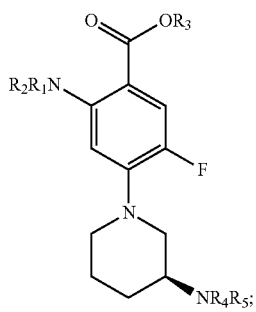
(III)

(b) converting said compound of Formula (III) to a compound of Formula (V)

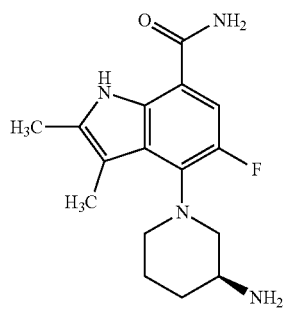
(V)

by steps (b1), (b2), and (b3), in any order:
(b1) forming an indole group by reaction with a compound of Formula (IVa) or a compound of Formula (IVb):

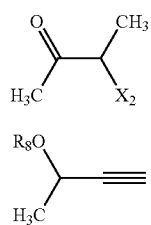
(IVa)

(IVb)

(b2) converting said —NR₄R₅ group to —NH₂; and
(b3) converting said —OR₃ group to —NH₂;
and
(c) reacting the compound of Formula (V) with a compound of Formula (VI)

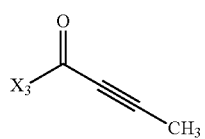
(VI)

to provide said compound of Formula (VII);
wherein:
$X_1$ is halo, —NO₂, —OS(O)₂R, or —N₂⁺;
$X_2$ is Cl, Br, I, —OH, —OS(O)₂R, acyloxy, or trialkylsiloxy;
$X_3$ is —OH, halo, —OCH₃, —O(aryl), —OC(O)R, —OS(O)₂R, —OS(O)R, —OP(O)R₂, or —OP(O)(OR)₂;
$R_1$ and $R_2$ are independently selected from H, benzyl, substituted benzyl, 4-methoxyphenyl, acyl, —S(O)₂Ar, tert-butoxycarbonyl, or benzyloxycarbonyl;
$R_3$ is H, $C_{1-8}$ alkyl, aryl, or heteroaryl;
$R_4$ and $R_5$ are independently selected from H, benzyl, 4-methoxybenzyl, 4-methoxyphenyl, acyl, —SO)₂R, tert-butoxycarbonyl, or benzyloxycarbonyl;
$R_8$ is H, $C_{1-3}$ alkyl, or aryl; and
each R is independently $C_{1-3}$ alkyl or aryl.

The third aspect of the invention provides a compound have the structure of Formula (Va):

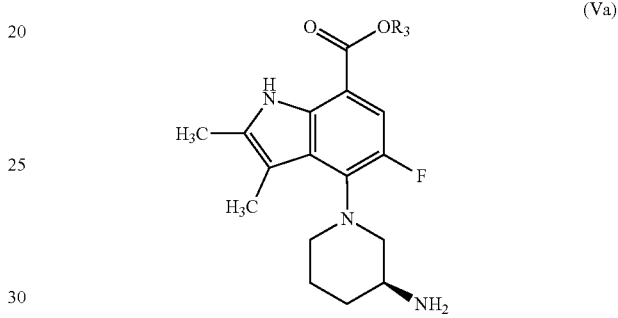
(Va)

or a salt thereof, wherein:
$R_3$ is $C_{1-6}$ alkyl unsubstituted or substituted with one or more $R_a$, benzyl unsubstituted or substituted with one or more $R_a$, or silyl; and each $R_a$ is independently F or Cl. This compound is useful as an intermediate in the processes of the first aspect and the second aspect.

The first step in the processes of the first aspect and the second aspect of this invention is the step of reacting a compound of Formula (I) and a compound of Formula (II) to provide a compound of Formula (III):

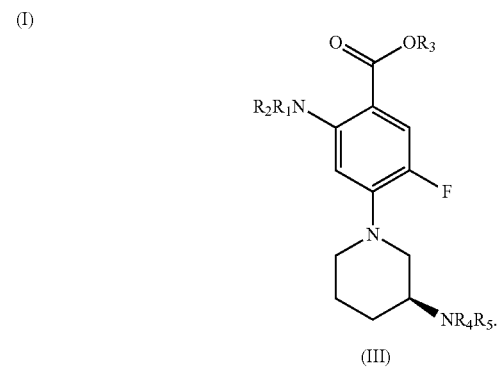

The compound of Formula (III) can be isolated and purified prior to use in the next synthetic step.

The first aspect and the second aspect of this invention include the step of converting the compound of Formula (III) to the compound of Formula (V):

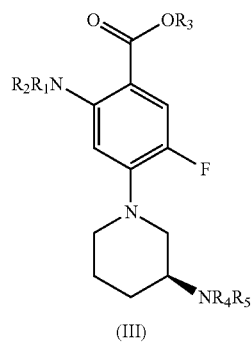

(III)

indolization
deprotection
amidation

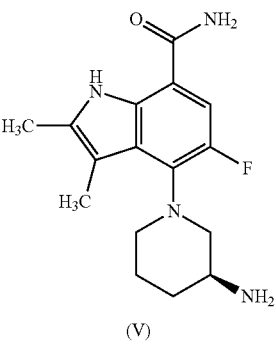

(V)

The preparation of the compound of Formula (V) from the compound of Formula (III) comprises the steps of:

Step (b1)—indolization by reacting a compound of Formula (III) with a compound of Formula (IVa) or a compound of Formula (IVb)

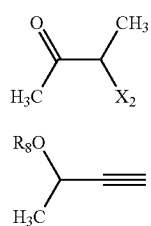

(IVa)

(IVb)

to form the indole group in the compound of Formula (V);

Step (b2)—deprotecting the —NR$_4$R$_5$ amine group attached to the piperidinyl ring of the compound of Formula (III) to form a primary amine group (—NH$_2$); and Step (b3)—amidating the indole ring in the compound of Formula (V) by converting the —OR$_3$ group to —NH$_2$. These three steps can be conducted in any order, either consecutively or concurrently.

In one embodiment, the compound of Formula (V) is prepared from the compound of Formula (III) according to the following reaction sequence:

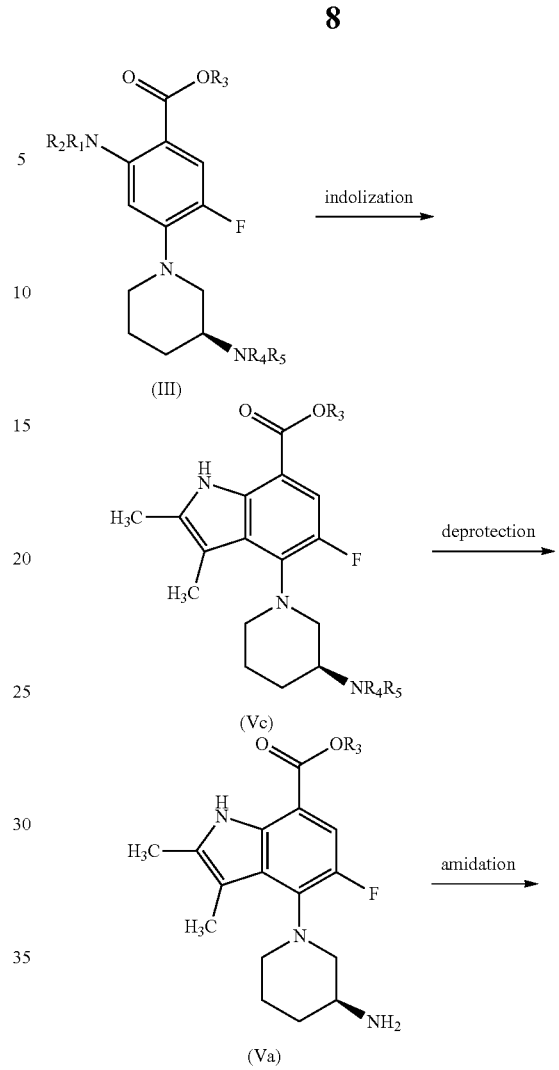

(III)

indolization (Vc)

deprotection (Va)

amidation

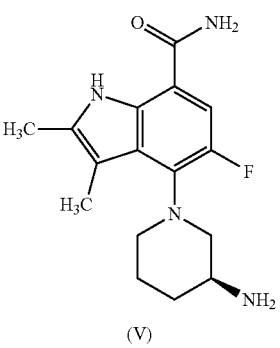

(V)

The steps of this embodiment comprise: Step (b1)—indolization by reacting a compound of Formula (III) with a compound of Formula (IVa) or a compound of Formula (IVb) to form the indole group in the compound of Formula (Vc); Step (b2)—deprotecting the —NR$_4$R$_5$ amine group attached to the piperidinyl ring of the compound of Formula (Vc) to form a primary amine group in the compound of Formula (Va); and Step (b3)—amidating the indole ring in the compound of Formula (Va) by converting the —OR$_3$ group to —NH$_2$ to provide the compound of Formula (V).

In one embodiment, the compound of Formula (V) is prepared from the compound of Formula (III) according to the following reaction sequence:

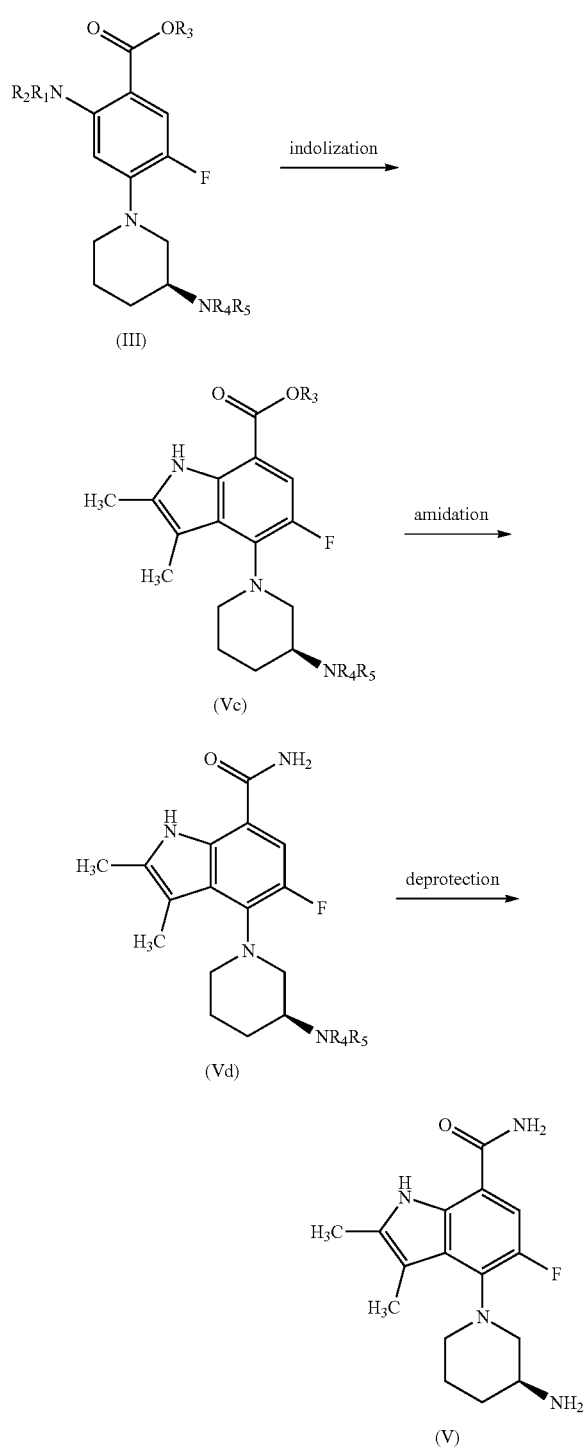

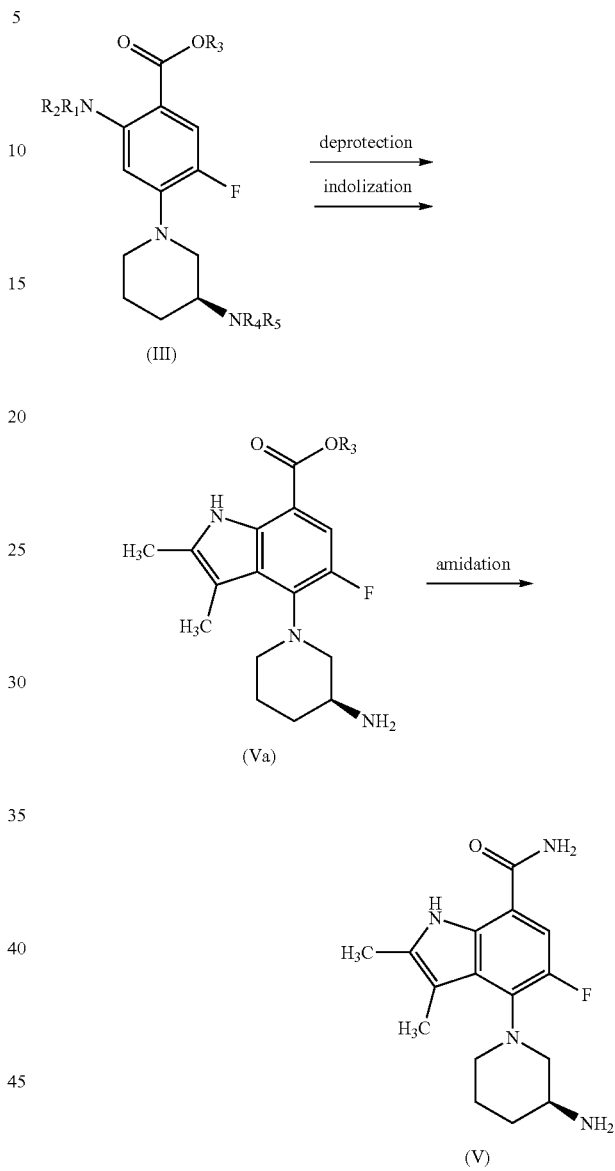

The steps of this embodiment comprise: Step (b1)—indolization by reacting a compound of Formula (III) with a compound of Formula (IVa) or a compound of Formula (IVb) to form the indole group in the compound of Formula (Vc); Step (b3)—amidating the indole ring in the compound of Formula (Vc) by converting the —OR$_3$ group to —NH$_2$ to provide the compound of Formula (Vd); and Step (b2)—deprotecting the —NR$_4$R$_5$ amine group attached to the piperidinyl ring of the compound of Formula (Vd) to form a primary amine group in the compound of Formula (V).

In one embodiment, the compound of Formula (V) is prepared from the compound of Formula (III) according to the following reaction sequence:

The steps of this embodiment comprise: Step (b1) and Step (b2)—indolization by reacting a compound of Formula (III) with a compound of Formula (IVa) or a compound of Formula (IVb) to form the indole group and deprotecting the —NR$_4$R$_5$ amine group attached to the piperidinyl ring to form the primary amine group to provide the compound of Formula (Va); and Step (b3)—amidating the indole ring in the compound of Formula (Va) by converting the —OR$_3$ group to —NH$_2$ to provide the compound of Formula (V). Step (b1) and Step (b2) are conducted concurrently or in a combination of concurrently and sequentially.

In one embodiment, the compound of Formula (V) is prepared from the compound of Formula (III) according to the following reaction sequence:

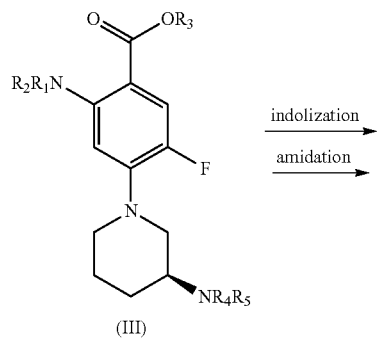

(III)

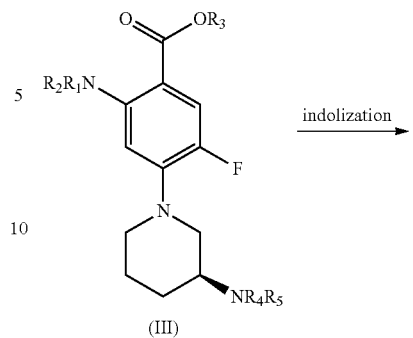

(III)

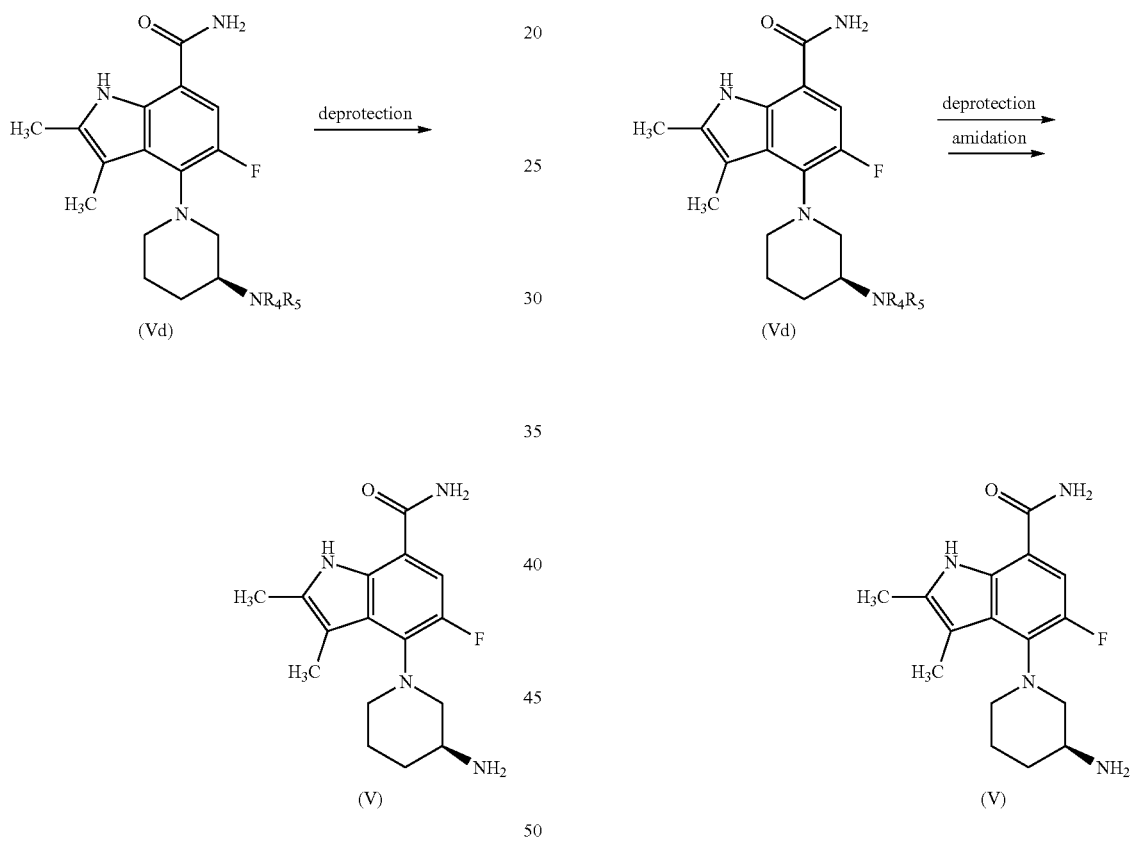

The steps of this embodiment comprise: Step (b1) and Step (b3)—indolization by reacting a compound of Formula (III) with a compound of Formula (IVa) or a compound of Formula (IVb) to form the indole group and converting the —OR₃ group to —NH₂ to provide the compound of Formula (Vd); and deprotecting the —NR₄R₅ amine group attached to the piperidinyl ring to form the primary amine group to provide the compound of Formula (V). Step (b1) and Step (b3) are conducted concurrently or in a combination of concurrently and sequentially.

In one embodiment, the compound of Formula (V) is prepared from the compound of Formula (III) according to the following reaction sequence:

The steps of this embodiment comprise: Step (b1)—indolization by reacting a compound of Formula (III) with a compound of Formula (IVa) or a compound of Formula (IVb) to form the indole group in the compound of Formula (Vc); and Step (b2) and Step (b3)—deprotecting the —NR₄R₅ amine group attached to the piperidinyl ring and amidating the indole ring by converting the —OR₃ group to —NH₂ to provide the compound of Formula (V). Step (b2) and Step (b3) are conducted concurrently or in a combination of concurrently and sequentially.

In one embodiment, the compound of Formula (V) is prepared from the compound of Formula (III) according to the following reaction sequence:

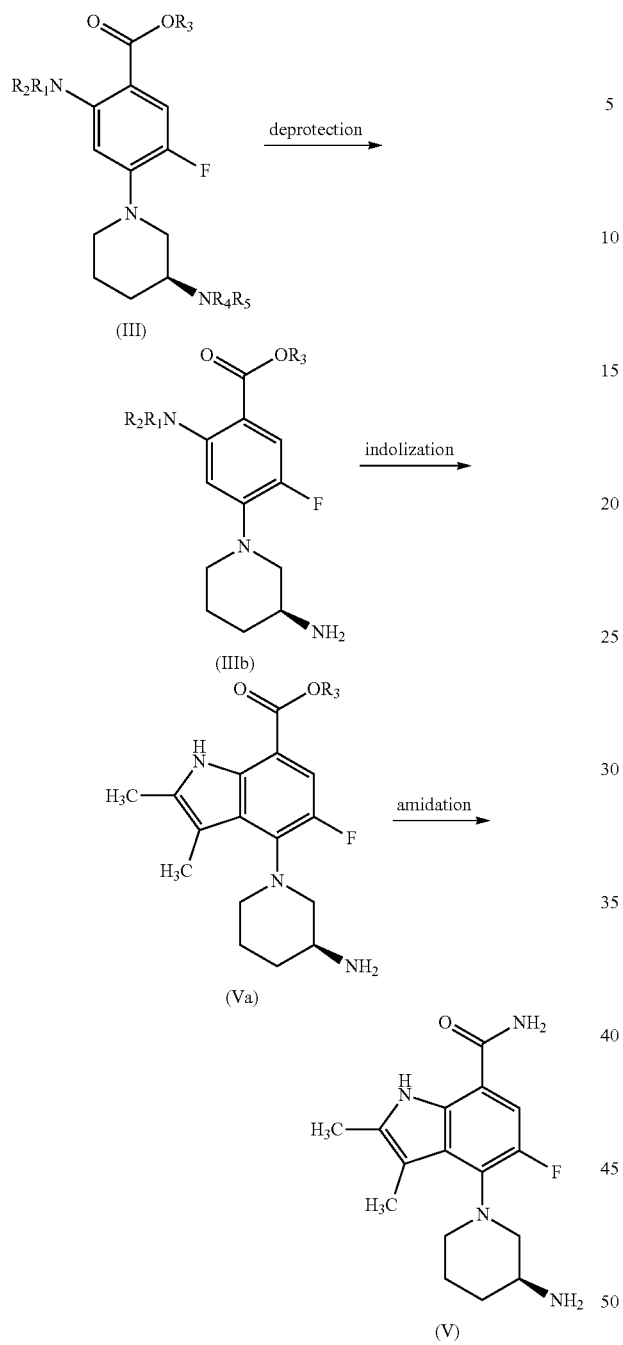

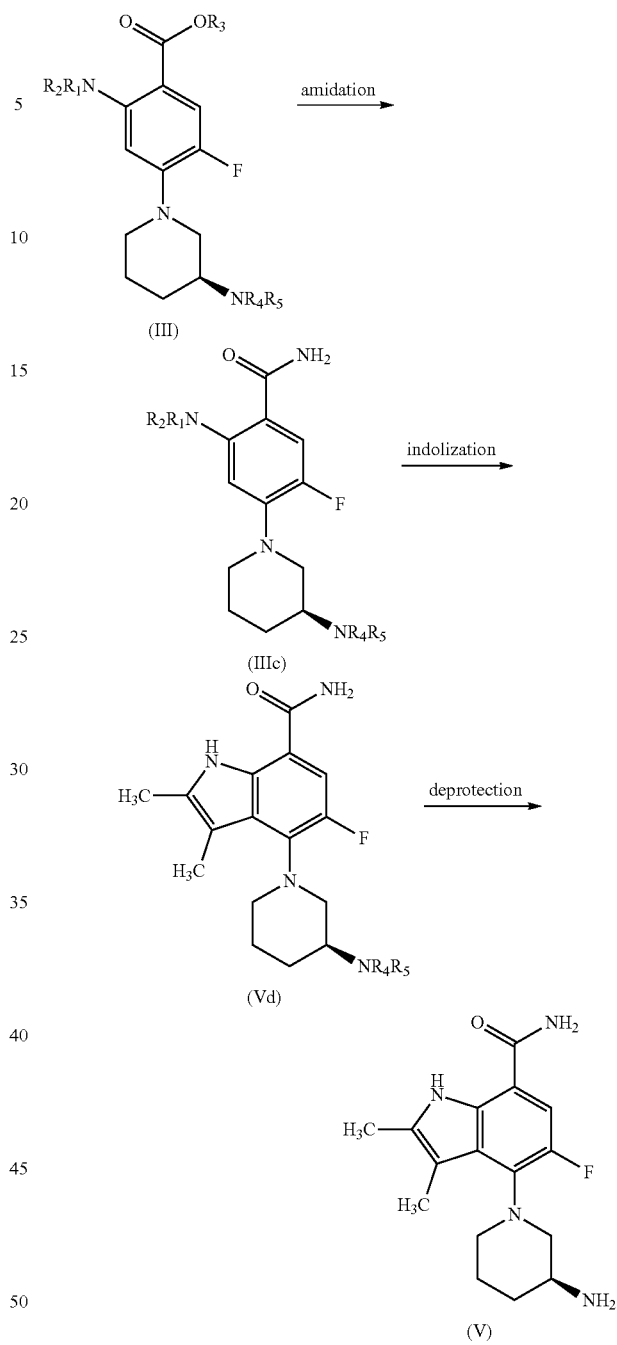

The steps of this embodiment comprise: Step (b2)—deprotecting the —NR$_4$R$_5$ amine group attached to the piperidinyl ring of the compound of Formula (III) to form a primary amine group in the compound of Formula (IIIb); Step (b1)—indolization by reacting a compound of Formula (IIIb) with a compound of Formula (IVa) or a compound of Formula (IVb) to form the indole group in the compound of Formula (Va); and Step (b3)—amidating the indole ring in the compound of Formula (Va) by converting the —OR$_3$ group to —NH$_2$ to provide the compound of Formula (V).

In one embodiment, the compound of Formula (V) is prepared from the compound of Formula (III) according to the following reaction sequence:

The steps of this embodiment comprise: Step (b3)—amidating the phenyl ring in the compound of Formula (III) by converting the —OR$_3$ group to —NH$_2$ to provide the compound of Formula (IIIc); Step (b1)—indolization by reacting a compound of Formula (IIIc) with a compound of Formula (IVa) or a compound of Formula (IVb) to form the indole group in the compound of Formula (Vd); Step (b2)—deprotecting the —NR$_4$R$_5$ amine group attached to the piperidinyl ring of the compound of Formula (Vd) to form a primary amine group in the compound of Formula (V).

In one embodiment, the compound of Formula (V) is prepared from the compound of Formula (III) according to the following reaction sequence:

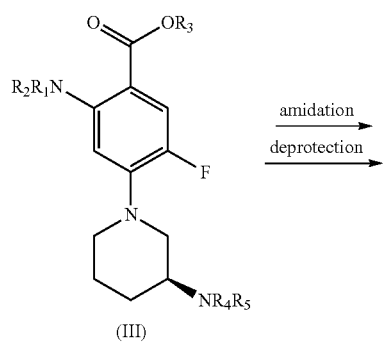

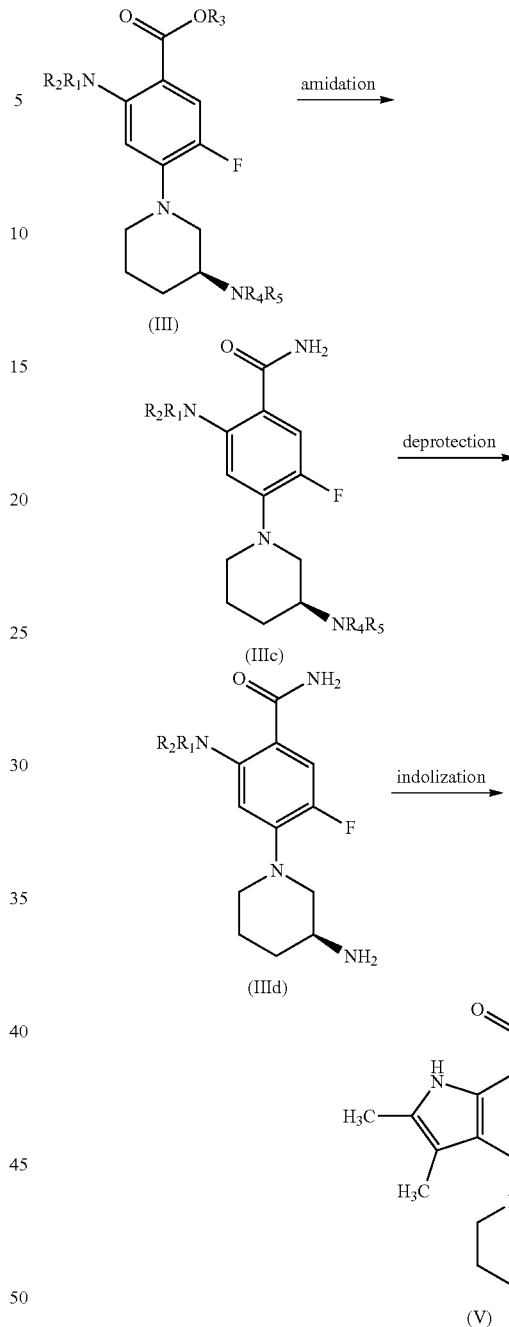

The steps of this embodiment comprise: Step (b2) and Step (b3)—deprotecting the —NR$_4$R$_5$ amine group attached to the piperidinyl ring to form the primary amine group and converting the —OR$_3$ group to —NH$_2$ to provide the compound of Formula (IIId); and indolization by reacting a compound of Formula (IIId) with a compound of Formula (IVa) or a compound of Formula (IVb) to form the indole group and provide the compound of Formula (V). Step (b2) and Step (b3) are conducted concurrently or in a combination of concurrently and sequentially.

In one embodiment, the compound of Formula (V) is prepared from the compound of Formula III according to the following reaction sequence:

The steps of this embodiment comprise: Step (b3)—amidating the phenyl ring in the compound of Formula (III) by converting the —OR$_3$ group to —NH$_2$ to provide the compound of Formula (IIIc); Step (b2)—deprotecting the —NR$_4$R$_5$ amine group attached to the piperidinyl ring of the compound of Formula (IIIc) to form a primary amine group in the compound of Formula (IIId); and Step (b1)—indolization by reacting a compound of Formula (IIId) with a compound of Formula (IVa) or a compound of Formula (IVb) to form the indole group in the compound of Formula (V).

In one embodiment, the compound of Formula (V) is prepared from the compound of Formula (III) according to the following reaction sequence:

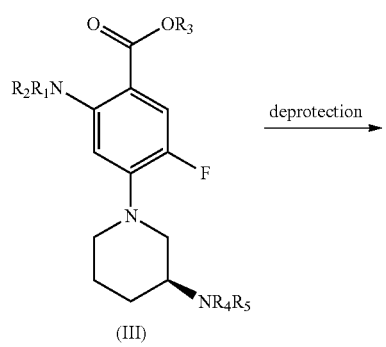

(III)

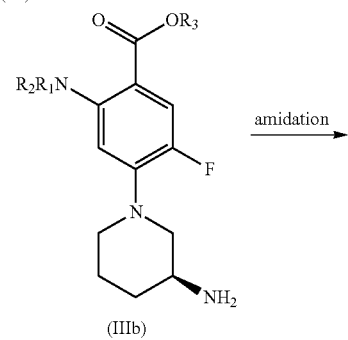

(IIIb)

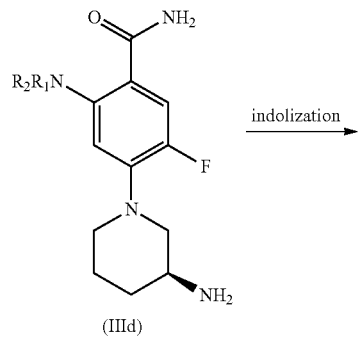

(IIId)

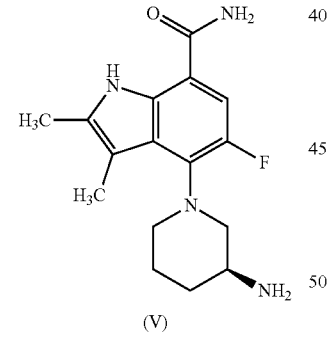

(V)

The steps of this embodiment comprise: Step (b2)—deprotecting the —NR$_4$R$_5$ amine group attached to the piperidinyl ring of the compound of Formula (III) to form a primary amine group in the compound of Formula (IIIc); Step (b3)—amidating the phenyl ring in the compound of Formula (IIIb) by converting the —OR$_3$ group to —NH$_2$ to provide the compound of Formula (IIId); and Step (b1)—indolization by reacting a compound of Formula (IIId) with a compound of Formula (IVa) or a compound of Formula (IVb) to form the indole group in the compound of Formula (V).

In Step (b3), the —OR$_3$ group is converted to —NH$_2$. This step can proceed directly or alternatively, can proceed through one or more intermediates. An indirect process for Step (b3) includes converting the —OR$_3$ group to —NR$_6$R$_7$, and then converting the —NR$_6$R$_7$ group to —NH$_2$, wherein R$_6$ and R$_7$ are individually selected from H, benzyl, 4-methoxybenzyl 4-methoxyphenyl, allyl, acyl, formyl, —OH, —OR, tert-butoxycarbonyl, benzyloxycarbonyl, and —S(O)$_2$R, provided that at least one of R$_6$ and R$_7$ is not H. Examples of indirect processes for (b3) include:

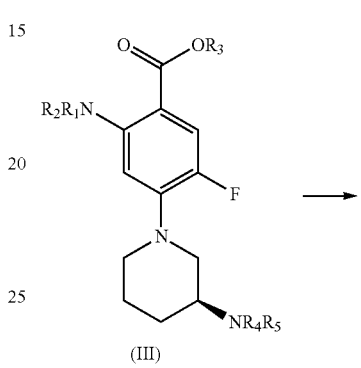

(III)

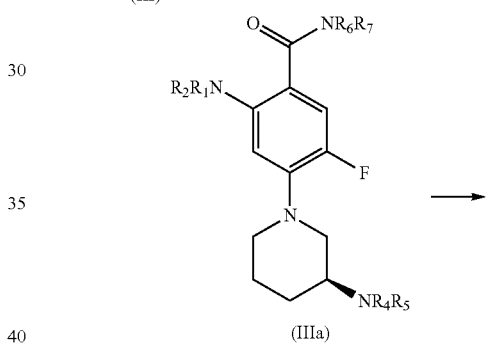

(IIIa)

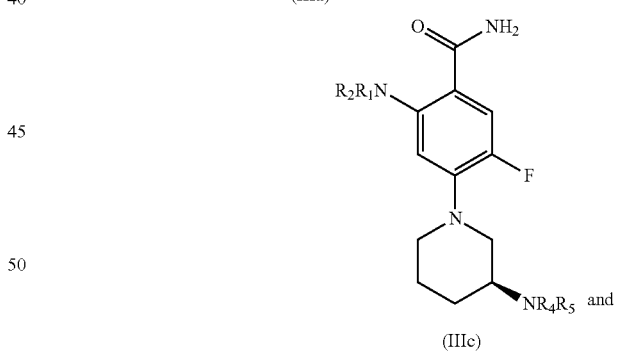

(IIIc)

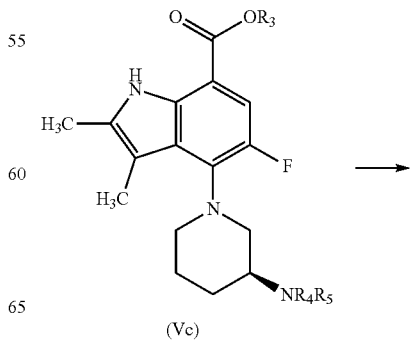

(Vc)

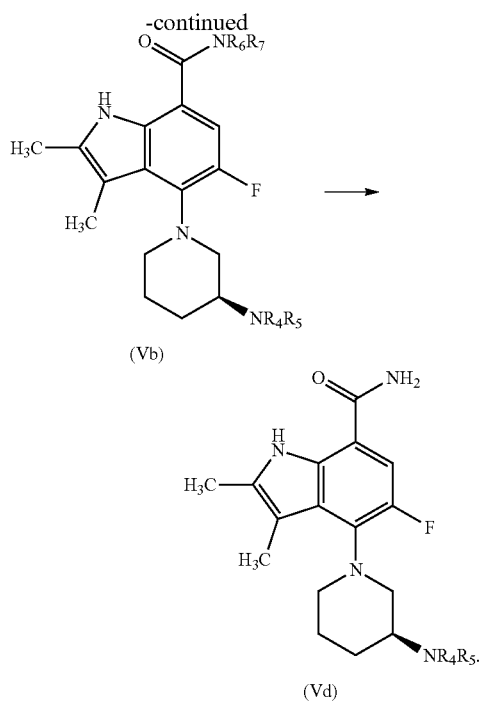

(Vb)

(Vd)

In one embodiment, a process of the first aspect or the second aspect is provided in which a compound of Formula (IVa) is used in Step (b1). Included in this embodiment is a process in which $X_2$ is Cl, Br, I, —OH, acyloxy, or trialkylsiloxy. Included in this embodiment is a process in which $X_2$ is Cl, Br, I, or —OH.

In one embodiment, a process of the first aspect or the second aspect is provided in which a compound of Formula (IVb) is used in Step (b1). Included in this embodiment is a process in which $R_8$ is H or $C_{1-3}$ alkyl. Also included in this embodiment is a process in which $R_8$ is H or —CH$_3$.

In one embodiment, a process of the first aspect or the second aspect is provided in which a compound of Formula (IVb) is used in Step (b1) and $R_8$ is aryl. Included in this embodiment is a process in which $R_8$ is phenyl.

In one embodiment, a process of the first aspect or the second aspect is provided in which $X_1$ is halo, —NO$_2$, —OS(O)$_2$R; and R is $C_{1-3}$ alkyl. Included in this embodiment is a process in which $X_1$ is halo. Also included in this embodiment is a process in which $X_1$ is F, Cl, or Br.

In one embodiment, a process of the first aspect or the second aspect is provided in which $X_2$ is Cl, Br, I, —OH, —OS(O)$_2$R, acyloxy, or trialkylsiloxy; and R is $C_{1-3}$ alkyl or aryl. Included in this embodiment is a process in which $X_2$ is —OH, Cl, Br, or I. Also included in this embodiment is a process in which $X_2$ is —OH.

In one embodiment, a process of the first aspect or the second aspect is provided in which $R_2$ is H or benzyl. Included in this embodiment are processes in which $R_2$ is H.

In one embodiment, a process of the first aspect or the second aspect is provided in which $R_3$ is H or —CH$_3$. Included in this embodiment are processes in which $R_3$ is —CH$_3$.

In one embodiment, a process of the first aspect or the second aspect is provided in which $R_4$ is H; and $R_5$ is benzyl, tert-butoxycarbonyl, or benzyloxycarbonyl. Included in this embodiment is a process in which $R_4$ is H; and $R_5$ is tert-butoxycarbonyl or benzyloxycarbonyl.

In one embodiment, a process of the first aspect or second aspect is provided in which $R_1$ is H; $R_2$ is H; $R_3$ is —CH$_3$; $R_4$ is H; $R_5$ is tert-butoxycarbonyl; $X_1$ is F; and $X_2$ is —OH.

In one embodiment, a process of the first aspect or second aspect is provided in which the compound of Formula (III) is provided wherein $R_1$ is H; $R_2$ is H; $R_4$ is H; and $R_5$ is H. In this embodiment, the compound of Formula (III) can be provided as an acid salt. Suitable acid salts of the compound of Formula (III) include salts formed from HCl, HBr, H$_2$SO$_4$, tartaric acid, fumaric acid, and boric acid.

In one embodiment, a process of the first aspect or second aspect is provided in which the compound of Formula (Vc) is provided wherein $R_4$ is H; and $R_5$ is H. In this embodiment, the compound of Formula (Vc) can be provided as an acid salt. Suitable acid salts of the compound of Formula (Vc) include salts formed from diphenylphosphoric acid and hydrochloric acid.

In one embodiment, a process of the first aspect or second aspect is provided in which the compound of Formula (V) is provided as an acid salt. Included in this embodiment is the compound of Formula (V) provided as an acid salt formed from HCl.

Step (a): Process for Preparing the Compound of Formula (III)

Various synthetic conditions can be employed to prepare a compound of Formula (III) by reacting the compound of Formula (I) and the compound of Formula (II). The reaction between the compound of Formula (I) and the compound of Formula (II) can be conducted in the presence of various synthesis adjuvants, including, for example, organic bases such as diisopropylethylamine, pyridine, dicyclohexylmethylamine, 2,6-lutidine, dimethylaminopyridine, diazabicyclooctane, and 1-methylimidazole, inorganic bases, such as dibasic potassium phosphate, calcium acetate, calcium carbonate, potassium carbonate, potassium bicarbonate, lithium acetate, lithium carbonate, magnesium acetate, magnesium carbonate, sodium carbonate, sodium bicarbonate, and potassium phosphate. Other synthesis adjuvants include nucleophilic catalysts like 4-dimethylaminopyridine and diazabicyclooctane; and transition metal catalysts like Pd, Ni, or Cu with or without appropriate ligands.

The reaction between the compound of Formula (I) and the compound of Formula (II) to provide the compound of Formula (III) can be conducted in various solvents or mixtures thereof. Examples of suitable solvents include, but are not limited to polar aprotic solvents such as dimethyl formamide, dimethyl sulfoxide, dimethylacetamide, sulfolane, tetramethylurea, and N-methylpyrrolidinone; etheral solvents such tetrahydrofuran, 2-methyl tetrahydrofuran, cyclopentyl methyl ether, dioxane, anisole, and diethoxymethane; halogenated solvents such as chlorobenzene, trifluorotoluene, and 1,2-dichlorobenzene; ester solvents such as ethyl acetate, isopropyl acetate, and butyl acetate; alcoholic solvents such as tert-amyl alcohol and 1-propanol; and other solvents such as acetonitrile, toluene, and cyclohexanone; and mixtures thereof. Preferred solvents include polar aprotic solvents such as dimethyl formamide, dimethyl sulfoxide, dimethylacetamide, sulfolane, tetramethylurea, and N-methylpyrrolidinone; etheral solvents such tetrahydrofuran, 2-methyl tetrahydrofuran, cyclopentyl methyl ether, dioxane, anisole, and diethoxymethane; and alcoholic solvents such as tert-amyl alcohol and 1-propanol. More preferred solvents include polar aprotic solvents such as dimethyl formamide, dimethyl sulfoxide, dimethylacetamide, sulfolane, tetramethylurea, and N-methylpyrrolidinone.

Suitable reaction temperatures for the reaction between the compound of Formula (I) and the compound of Formula (II) include temperatures in the range of from about 40° C. to about 140° C., preferably in the range of from about 60° C. to about 120° C., and more preferably, from about 90° C. to about 110° C.

The compound of Formula (III) can be isolated and/or purified by various methods known in the art. Suitable methods include chromatography, crystallization, filtration, and distillation.

Step (b): Process for Preparing the Compound of Formula (V)

The process for converting the compound of Formula (III) to the compound of Formula (V) comprises three steps including indolization (Step (b1)), deprotecting the piperidinyl —$NR_4R_5$ amine group (Step (b2)); and amidation by converting the —$OR_3$ group to —$NH_2$ (Step (b3)). These three steps can be conducted in any order, either consecutively or concurrently.

Various synthetic conditions can be employed in each of these three reactions.

The indolization reaction of Step (b1) can be conducted in the presence of various synthesis adjuvants, including, for example, diphenylphosphoric acid, dibenzylphosphoric acid, diphenylphosphinic acid, hydrochloric acid, hydrobromic acid, methanesulfonic acid, trifluoromethanesulfonic acid, trifluoroacetic acid, p-toluenesulfonic acid, benzenesulfonic acid, sulfuric acid, phosphoric acid, trichloroacetic acid, tin(II) chloride, tin(II) triflate, ytterbium triflate, aluminum triflate, bismuth triflate, zirconium chloride, titanium chloride, scandium triflate, and iron(III) triflate The reaction of Step (b1) can be conducted in various solvents or mixtures thereof. Examples of suitable solvents include, but are not limited to, ethereal solvents such as methyl-tetrahydrofuran (Me-THF), tetrahydrofuran (THF), dioxane, diglyme, and anisole; hydrocarbon solvents such as toluene; halogenated solvents such as trifluorotoluene and chlorobenzene; alcoholic solvents such as isopropanol; ester solvents such as isopropyl acetate and butyl acetate; and other solvents such as acetic acid or acetonitrile; and mixtures thereof. Preferred solvents include ethereal solvents such as Me-THF, THF, dioxane, diglyme, and anisole; and hydrocarbon solvents such as toluene. More preferred solvents include hydrocarbon solvents such as toluene.

Suitable reaction temperatures for the Step (b1) reaction include temperatures in the range of from about 40° C. to about 100° C., preferably in the range of from about 50° C. to about 90° C., and more preferably, from about 60° C. to about 80° C.

The deprotecting reaction of Step (b2) can be conducted in the presence of various synthesis adjuvants, including, for example, diphenylphosphoric acid, dibenzylphosphoric acid, diphenylphosphinic acid, hydrochloric acid, hydrobromic acid, methanesulfonic acid, trifluoromethanesulfonic acid, trifluoroacetic acid, p-toluenesulfonic acid, benzenesulfonic acid, sulfuric acid, phosphoric acid, trichloroacetic acid, tin(II) chloride, tin(II) triflate, ytterbium triflate, aluminum triflate, bismuth triflate, zirconium chloride, titanium chloride, scandium triflate, and iron(III) triflate.

The reaction of Step (b2) can be conducted in various solvents or mixtures thereof. Examples of suitable solvents include, but are not limited to, ethereal solvents such as Me-THF, THF, dioxane, diglyme, and anisole; hydrocarbon solvents such as toluene; halogenated solvents such as trifluorotoluene and chlorobenzene; alcoholic solvents such as isopropanol; ester solvents such as isopropyl acetate and butyl acetate; and other solvents such as acetic acid or acetonitrile; and mixtures thereof. Preferred solvents include ethereal solvents such as Me-THF, THF, dioxane, diglyme, and anisole; and hydrocarbon solvents such as toluene. More preferred solvents include hydrocarbon solvents such as toluene.

Suitable reaction temperatures for the Step (b2) reaction include temperatures in the range of from about 40° C. to about 100° C., preferably in the range of from about 50° C. to about 90° C., and more preferably, from about 60° C. to about 80° C.

The amidation reaction of Step (b3) can be conducted in the presence of various synthesis adjuvants, including, for example, sodium formamide or 1,5,7-triazabicyclo[4.4.0]dec-5-ene. The reaction of Step (b3) can be conducted in various solvents or mixtures thereof. Examples of suitable solvents include, but are not limited to, ethereal solvents like THF and Me-THF; polar aprotic solvents like dimethylformamide; alcoholic solvents like methanol; and mixtures thereof.

Suitable reaction temperatures for the Step (b3) reaction between the compound of Formula (I) and the compound of Formula (II) include temperatures in the range of from about 0° C. to about 100° C., preferably in the range of from about 10° C. to about 90° C., and more preferably, from about 20° C. to about 80° C.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-3}$ alkyl" denotes straight and branched chain alkyl groups with one to three carbon atoms.

The term "aryl" as used herein, refers to a group of atoms derived from a molecule containing aromatic ring(s) by removing one hydrogen that is bonded to the aromatic ring(s). Heteroaryl groups that have two or more rings must include only aromatic rings. Representative examples of aryl groups include, but are not limited to, phenyl and naphthyl. The aryl ring may be unsubstituted or may contain one or more substituents as valence allows. Exemplary substituents include F, Cl, Br, I, —OH, $C_{1-6}$ alkyl, $C_{1-4}$ fluoroalkyl, —$NO_2$, —$NH_2$, and —O($C_{1-3}$ alkyl).

The term "benzyl," as used herein, refers to a methyl group in which one of the hydrogen atoms is replaced by a phenyl group. The phenyl ring may be unsubstituted or may contain one or more substituents as valence allows, including F, Cl, Br, I, —OH, $C_{1-6}$ alkyl, $C_{1-4}$ fluoroalkyl, —$NO_2$, —$NH_2$, and —O($C_{1-3}$ alkyl).

The compounds of Formulas (I), (II), (III), (Vc), and (V) can form acid salts which are also within the scope of this invention. Unless otherwise indicated, reference to an inventive compound is understood to include reference to one or more salts thereof. The term "salt(s)" denotes acidic salts formed with inorganic and/or organic acids. Pharmaceutically acceptable (i.e., non-toxic, physiologically acceptable) salts are preferred. However, other salts may be useful, e.g., in isolation or purification steps which may be employed during preparation, and thus, are contemplated within the scope of the invention. Salts of the compounds of the Formulas (I), (II), (III), (Vc), or (V) may be formed, for example, by reacting a compound of the Formulas (I), (II), (III), (Vc), or (V) with an amount of acid, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formulas (I), (II), (III), (IV), (V), and (VII) can be provided as amorphous solids or crystalline solids. Lyophilization can be employed to provide the compounds as a solid.

It should further be understood that solvates (e.g., hydrates) of the compounds of Formulas (I), (II), (III), (IV), (V), and (VII) are also within the scope of the present invention. The term "solvate" means a physical association of a compound of Formulas (I), (II), (III), (IV), (V), or (VII) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of Formulas (I), (II), (III), (IV), (V), and (VII), subsequent to their preparation, can be isolated and purified to obtain a composition containing an amount by weight equal to or greater than 99% of a compound of Formulas (I), (II), (III), (IV), (V), and (VII) ("substantially pure"), which is then used or formulated as described herein. Such "substantially pure" compounds of Formulas (I), (II), (III), (IV), (V), and (VII) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH₃) also includes deuterated methyl groups such as —CD₃.

EXAMPLES

The invention is further defined in the following Example. It should be understood that the Example is given by way of illustration only. From the above discussion and the Example, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations anhyd. anhydrous
aq. aqueous
Bn benzyl
Boc tert-butoxycarbonyl
DMF dimethylformamide
DMSO dimethylsulfoxide
DPPOH diphenyl phosphate
Et ethyl
Et₃N triethyl amine
EtOH ethanol
H or H₂ hydrogen
h, hr or hrs hour(s)
IPA isopropyl alcohol
HPLC high pressure liquid chromatography
IPAc isopropyl acetate
LC liquid chromatography
LCMS liquid chromatography mass spectroscopy
M molar
mM millimolar
Me methyl
MeOH methanol
MeTHF methyl tetrahydrofuran
MHz megahertz
min. minute(s)
mins minute(s)
MS mass spectrometry
MTBE methyl tetrabutyl ether
NaOMe sodium methoxide
nM nanomolar
Ph phenyl
Ret Time or Rt retention time
sat. saturated
SFC supercritical fluid chromatography
TBD 1,3,4,6,7,8-hexahydro-2H-pyrimido[1,2-a]pyrimidine
t-BuOH tertiary butanol
TBTU O-(Benzotriazol-1-yl)-N,N,N',N'-tetramethyluronium tetrafluoroborate
THF tetrahydrofuran

Example 1

(S)-4-(3-(but-2-ynamido)piperidin-1-yl)-5-fluoro-2,3-dimethyl-1H-indole-7-carboxamide

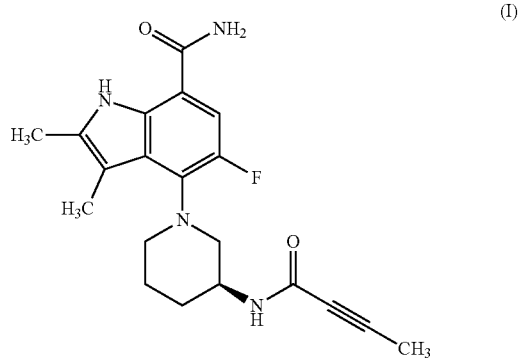 [SMILES: CC#CC(=O)N[C@H]1CCCN(c2c(F)cc(C(N)=O)c3[nH]c(C)c(C)c23)C1]

Step 1: Preparation of Methyl (S)-2-amino-4-(3-((tert-butoxycarbonyl)amino)piperidin-1-yl)-5-fluorobenzoate

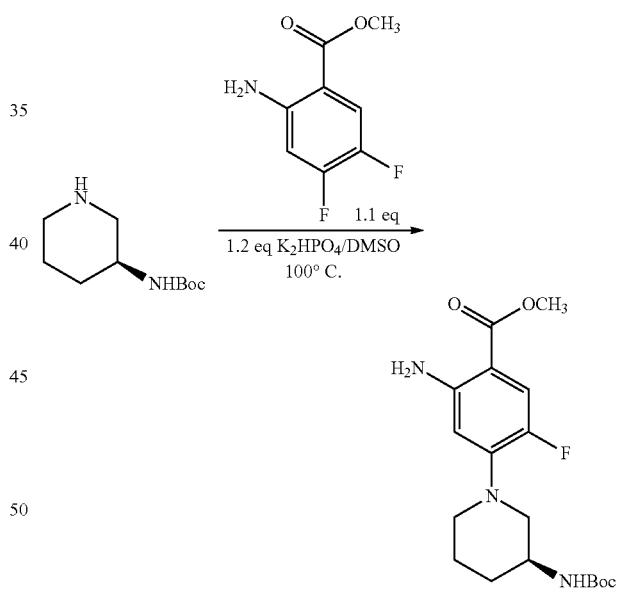

To a 250 mL ChemGlass reactor were charged methyl 2-amino-4,5-difluoro-benzoate (11.21 g, 59.90 mmol), tert-butyl N-[(3S)-3-piperidyl]carbamate (10 g, 49.930 mmol), potassium phosphate, dibasic (10.44 g, 59.94 mmol), and dimethylsulfoxide (100 mL, 1400 mmol). The resulting thin slurry was heated to 95 to 100° C. and agitated at this temperature for 25 hours. The mixture was cooled to 50° C. Methanol (100 mL) was added and followed by slow addition of water (50 mL). The mixture was aged at 50° C. for 30 minutes to result in a thick white slurry. Additional water (150 mL) was slowly charged to the above mixture and agitated at 50° C. for 1 hour. The slurry was cooled to 20° C. in 1 hour and aged at this temperature for 4 hours. The slurry was filtrated. The wet cake washed with 25% MeOH in water (30 mL), water (100 mL) and dried under vacuum at 60° C. for 24 h. Methyl (S)-2-amino-4-(3-((tert-butoxycarbonyl)amino) piperidin-1-yl)-5-fluorobenzoate was obtained as a white solid (7 g, yield: 72.5%). $^1$H NMR (400 MHz, METHANOL-d$_3$) δ 7.34 (d, J=14.6 Hz, 1H), 6.27 (d, J=7.3 Hz, 1H), 3.83-3.71 (s, 3H), 3.68-3.57 (m., 1H), 3.50-3.40 (m 1H), 3.39-3.31 (m, 1H), 3.31-3.26 (m, 1H), 2.86-2.70 (m, 1H), 2.64 (t, J=10.0 Hz, 1H), 1.97-1.84 (m, 1H), 1.84-1.74 (m, 1H), 1.73-1.61 (m, 1H), 1.44 (s, 9H), 1.38 (m, 1H). LC-MS [M+H] 368.

Step 2: Preparation of Methyl (S)-4-(3-aminopiperidin-1-yl)-5-fluoro-2,3-dimethyl-1H-indole-7-carboxylate

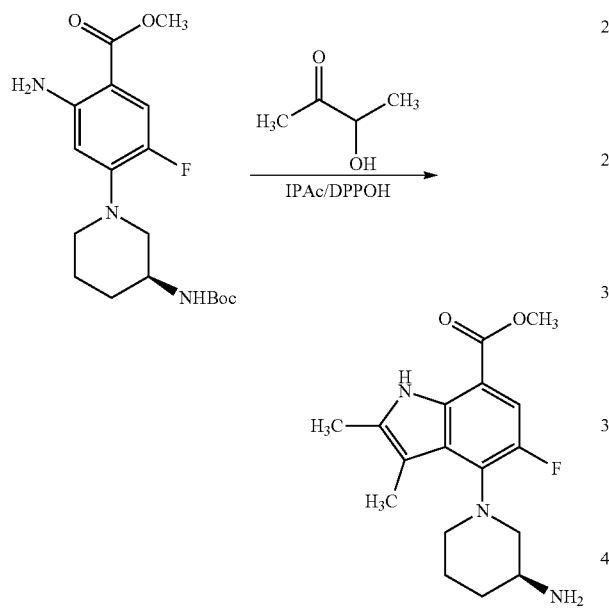

To a reactor were charged methyl (S)-2-amino-4-(3-((tert-butoxycarbonyl)amino) piperidin-1-yl)-5-fluorobenzoate (5.0 g), DPPOH (diphenyl phosphate, 6.81 g, 2 eq) and 3-hydroxybutanone (1.2 eq, 1.44 g), followed by addition of isopropyl acetate (100 mL, 20 mL/g). The mixture was allowed to warm up to 70 to 75° C., resulting in a yellow solution. The solution was stirred at 70 to 75° C. for 30 h to complete the cyclization. Water (2 mL) was added and the mixture was aged at 70° C. over 24 h to remove the Boc group. The mixture was cooled to room temperature. Next, aqueous 20% K$_3$PO$_4$ solution (50 mL) was added and the mixture was stirred for 15 min. The organic layer was separated and washed with water (50 mL). The organic layer was then concentrated under vacuum (200 Torr) to ~50 mL. The resulting slurry was stirred at 50° C. for 2 h and then heptane (100 mL) was added over 1 h. The mixture was cooled to room temperature, stirred for 20 h, and then filtered. The cake was washed with heptane (50 mL). Methyl (S)-4-(3-aminopiperidin-1-yl)-5-fluoro-2,3-dimethyl-1H-indole-7-carboxylate, DPPOH salt was obtained as a light yellow solid. The wet-cake was added to a reactor. Isopropyl acetate (100 mL) was added, followed by addition of aqueous K$_3$PO$_4$ solution (4 g in water 50 mL). The mixture was stirred at room temperature for ~half-hour, resulting in a two phase clear solution (pH>10 for aqueous). The organic layer was separated and washed with water (50 mL), and then concentrated under vacuum to a volume of 15 mL. The resulting slurry was stirred at room temperature for 4 h, then heptane (75 mL) was added over 1 h. The mixture was aged at room temperature for 24 h, then concentrated to a volume to ~50 mL. The slurry was filtered. The cake was washed with heptane 20 mL and dried under vacuum at 50° C. for 24 h. Methyl (S)-4-(3-aminopiperidin-1-yl)-5-fluoro-2,3-dimethyl-1H-indole-7-carboxylate was obtained as a light yellow solid (2.76 g, yield: 69%). $^1$H NMR (400 MHz, DMSO-d$_6$) δ 10.64 (s, 1H), 7.33 (d, J=13.7 Hz, 1H), 3.89 (s, 3H), 3.14 (br. m., 1H), 3.07-2.90 (m, 2H), 2.84 (br. m., 1H), 2.70 (br. m., 1H), 2.35 (s, 3H), 2.33 (s, 3H), 1.87 (br. m., 1H), 1.67 (br. m., 3H). LC-MS: M+H=320.

Alternative Preparation

Step 2: Preparation of ethyl (S)-4-(3-aminopiperidin-1-yl)-5-fluoro-2,3-dimethyl-1H-indole-7-carboxylate Trifluoroacetic Acid Salt

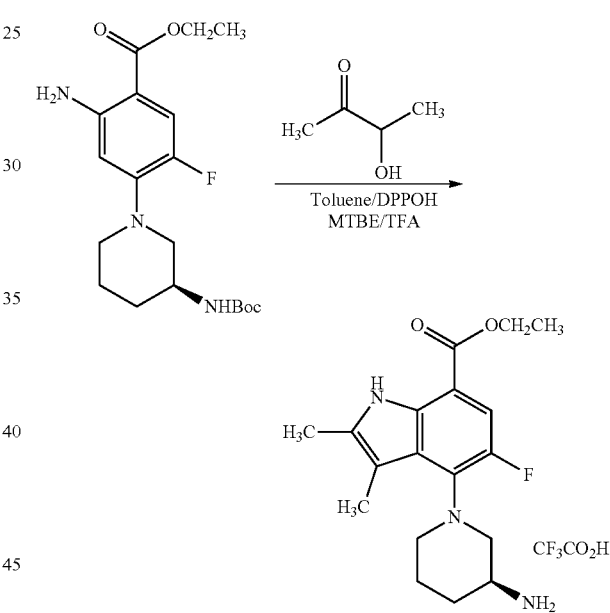

To a reactor were charged ethyl (S)-2-amino-4-(3-((tert-butoxycarbonyl)amino) piperidin-1-yl)-5-fluorobenzoate (1.0 g, limiting reagent), DPPOH (diphenyl phosphate, 1.97 g, 3.0 eq) and 3-hydroxybutanone (1.4 eq, 0.32 g), followed by addition of toluene (20 mL, 20 mL/g). The mixture was allowed to warm up to 80-90° C., resulting in a yellow solution. The solution was stirred at 80-90° C. for 10 h to complete the cyclization. Water (0.4 mL, 0.4 ml/g) was added and the mixture was aged at 80-90° C. for 8 hours. The mixture was cooled to room temperature. Next, aqueous 20% K$_3$PO$_4$ solution (15 mL, 15 mL/g) was added and the mixture was stirred for 0.5 hour. The organic layer was separated and the aqueous layer was washed with toluene (7.5 mL, 7.5 mL/g). To combined organic layers water (10 mL, 10 mL/g) was added and the mixture was stirred for 0.5 hour. The organic layer was separated. To the organic layer water (10 mL, 10 mL/g) was added and the mixture was stirred for 0.5 hour. The organic layer was separated. The organic layer was concentrated under vacuum (100 Torr) to 8 mL (8 ml/g). Following concentration the reaction mixture was cooled to 20-25° C. and MTBE (20 mL, 20 mL/g) was added. Trifluoroacetic acid (1.2 eq., 0.36 g) was slowly added to make the salt maintaining temperature at 20-25° C. The resulting slurry was aged for 4 hours and then filtered. The filtered solids are washed with MTBE (8 mL, 8 mL/g) and the cake was dried under vacuum at 50° C. (S)-4-(3-aminopiperidin-1-yl)-5-fluoro-2,3-dimethyl-1H-indole-7-carboxylate trifluoroacetic acid salt was obtained as a white to tan crystalline material (85% yield, 1.0 g). $^1$H NMR (400 MHz, DMSO-d$_6$) δ 10.74 (s, 1H), 8.16-7.88 (m, 2H), 7.37 (d, J=13.6 Hz, 1H), 4.38 (q, J=7.1 Hz, 2H), 3.18-3.01 (m, 3H), 2.96 (br s, 1H), 2.35 (s, 6H), 2.30 (s, 1H), 2.12 (br d, J=9.3 Hz, 1H), 1.78 (br s, 2H), 1.45-1.31 (m, 4H), 1.10 (s, 1H). $^{13}$C NMR (101 MHz, DMSO-d$_6$) δ 165.1, 165.1, 158.4, 158.1, 135.4, 134.7, 134.6, 132.2, 128.8, 128.2, 126.9, 126.8, 118.7, 115.7, 110.6, 110.3, 108.7, 108.6, 106.6, 106.5, 83.5, 79.8, 60.5, 54.9, 51.7, 48.7, 47.2, 28.4, 26.8, 23.6, 14.2, 11.1, 10.2

Step 3A: Preparation of (S)-4-(3-aminopiperidin-1-yl)-5-fluoro-2,3-dimethyl-1H-indole-7-carboxamide

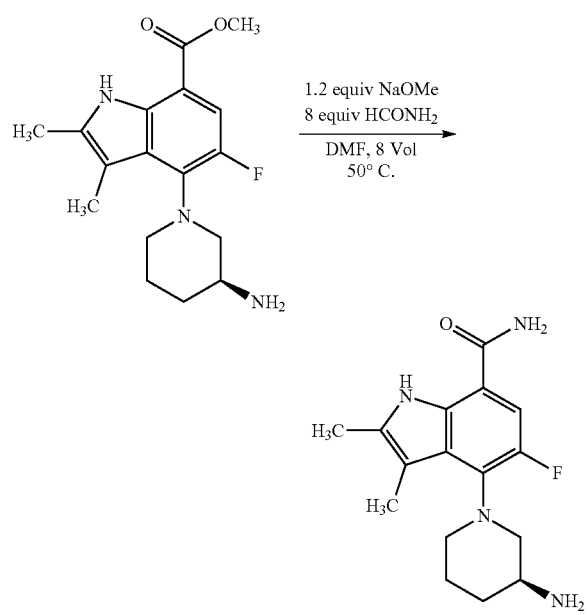

A 40 mL vial was charged with methyl (S)-4-(3-aminopiperidin-1-yl)-5-fluoro-2,3-dimethyl-1H-indole-7-carboxylate (1.5 g, 4.70 mmol), followed by the addition of N,N-dimethylformamide (12.0 mL, 8.0 mL/g). The vial was purged with N$_2$. Formamide (1.49 mL, 37.6 mmol) was added followed by sodium methoxide solution in methanol (35 wt %, 1.29 mL, 3.76 mmol). The resulting solution was heated at 50° C. over 8 hours. The reaction mixture was cooled down to room temperature and the reaction was quenched with water (12.0 mL, 8.0 mL/g). 2-methyltetrahydrofuran (30 mL, 20 mL/g) was added to the mixture. The mixture was shaken vigorously. The layers were separated and the aqueous layer was extracted with 2-methyltetrahydrofuran (15 mL, 10 mL/g) two more times. Organic extracts were then washed with brine and water (15 mL each, 10 mL/g). The organic layer was evaporated. Solids were dried in vacuo at 60° C. to afford (S)-4-(3-aminopiperidin-1-yl)-5-fluoro-2,3-dimethyl-1H-indole-7-carboxamide as a yellow solid (1.04 g, 69% yield). $^1$H NMR (500 MHz, DMSO-d$_6$) δ 10.60 (br. s., 1H), 7.91 (br. s., 1H), 7.40 (d, J=14.0 Hz, 1H), 7.32 (br. s., 1H), 3.10 (br. s., 1H), 2.98 (br. s., 2H), 2.82 (br. s., 1H), 2.68 (br. s., 1H), 2.34 (br. s., 3H), 2.30 (br. s., 3H), 1.88 (br. s., 1H), 1.67 (br. s., 2H), 1.45 (br. s., 2H), 1.05 (br. s., 1H). LCMS [M+H] 305.24.

Step 3B: Alternative Preparation of (S)-4-(3-aminopiperidin-1-yl)-5-fluoro-2,3-dimethyl-1H-indole-7-carboxamide

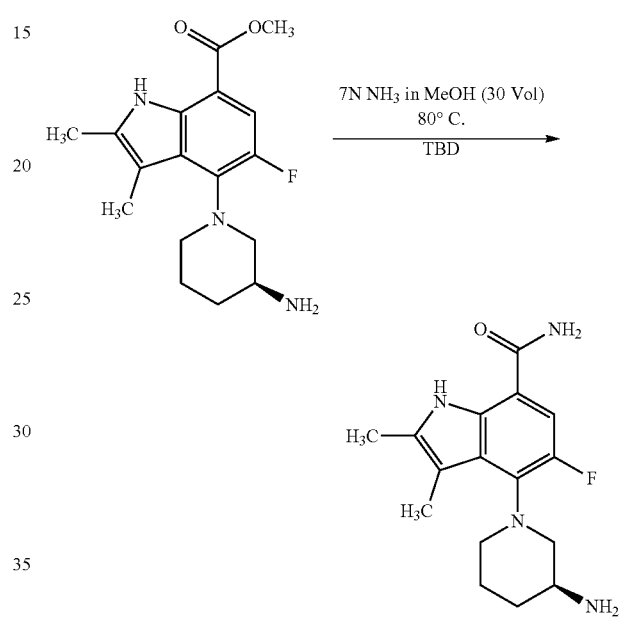

A 100 mL Hastelloy high pressure EasyMax reactor was charged with methyl (S)-4-(3-aminopiperidin-1-yl)-5-fluoro-2,3-dimethyl-1H-indole-7-carboxylate (1.5 g, 4.70 mmol), followed by addition of 7 N ammonia solution in methanol (45.0 mL, 30.0 mL/g) followed by addition of 1,3,4,6,7,8-hexahydro-2H-pyrimido[1,2-a]pyrimidine (1.33 g, 9.39 mmol). The reactor was sealed and purged with N$_2$ three times. The reactor was then heated to 80° C. for 24 hrs. The reaction mixture was cooled to room temperature and the vessel contents were purged with N$_2$ three times. Volatiles were concentrated to ~6 mL (4 mL/g) and water (24 mL, 16 mL/g) was added. The yellow precipitate was collected and filtered. The precipitate was washed with methanol/water mixture (20:80 v/v, 6 mL, 4 mL/g), and then water (18 mL, 12 mL/g). The solids were dried in vacuo at 60° C. to afford (S)-4-(3-aminopiperidin-1-yl)-5-fluoro-2,3-dimethyl-1H-indole-7-carboxamide as a yellow crystalline material (0.93 g, 62% yield). $^1$H NMR (500 MHz, DMSO-d$_6$) δ 10.60 (br. s., 1H), 7.91 (br. s., 1H), 7.40 (d, J=14.0 Hz, 1H), 7.32 (br. s., 1H), 3.10 (br. s., 1H), 2.98 (br. s., 2H), 2.82 (br. s., 1H), 2.68 (br. s., 1H), 2.34 (br. s., 3H), 2.30 (br. s., 3H), 1.88 (br. s., 1H), 1.67 (br. s., 2H), 1.45 (br. s., 2H), 1.05 (br. s., 1H). LCMS [M+H] 305.24.

Alternative Preparation

Step 3C: Preparation of (S)-4-(3-aminopiperidin-1-yl)-5-fluoro-2,3-dimethyl-1H-indole-7-carboxamide 2-butynoic Acid Salt

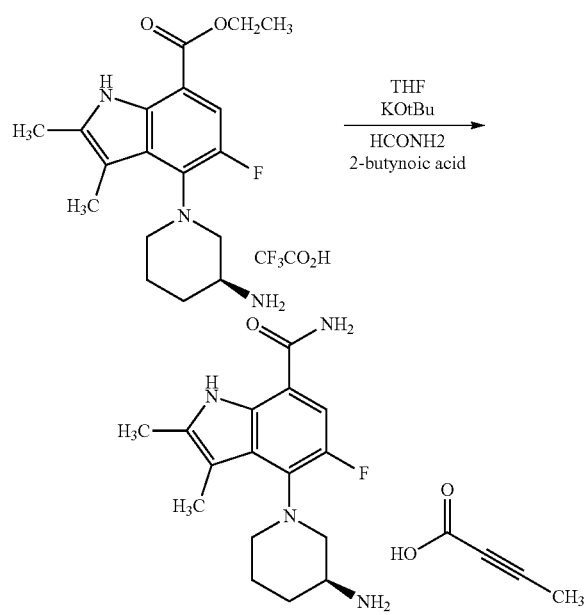

Ethyl (S)-4-(3-aminopiperidin-1-yl)-5-fluoro-2,3-dimethyl-1H-indole-7-carboxylate trifluoroacetic acid salt (1.0 g, limiting reagent) and formamide (5 mL, 5 mL/g) were added to a nitrogen inerted reactor. The temperature was maintained at 20-25° C. To the reactor was added a solution of 20 wt % potassium t-butoxide in THF. The reaction mixture was allowed to sit for 6 hours. To reaction mixture was added Me-THF (15 mL, 15 mL/g) and 12.5 wt % aqueous NaCl (5 mL, 5 mL/g). The reaction mixture was stirred for 0.5 hour. The organic layer was separated, 5 wt % aqueous NaCl (1 mL, 1 mL/g) and 0.25 N aqueous NaOH (4 mL, 4 mL/g) were added, and then stirred for 0.5 hour. The organic layer was separated and 5 wt % aqueous NaCl (5 mL, 5 mL/g) was added, the mixture was stirred for 0.5 hour, and organic phase was separated. The rich organic phase was dried distillation at a pressure of 100 mtorr with Me-THF to obtain KF in 1.5-4 wt % range at 5 mL Me-THF volume. The volume was adjusted to 15 mL Me-THF by adding Me-THF (10 mL, 10 mL/g) and EtOH (4 mL, 4 mL/g). Next, 2-butynoic acid (1.0 eq., 0.19 g) was added and the mixture was agitated for 10 hrs. The resulting slurry was filtered. The cake was washed with Me-THF (10 mL, 10 mL/g) and dried under vacuum at 75° C. to afford (S)-4-(3-aminopiperidin-1-yl)-5-fluoro-2,3-dimethyl-1H-indole-7-carboxamide 2-butynoic acid salt (0.7 g, 80% yield) as white crystalline powder. $^1$H NMR (400 MHz, DMSO-$d_6$) δ 10.68 (s, 1H), 7.98 (br s, 1H), 7.50-7.32 (m, 2H), 3.32 (br d, J=8.6 Hz, 2H), 3.21 (br t, J=10.5 Hz, 1H), 3.13-2.89 (m, 3H), 2.32 (d, J=5.1 Hz, 5H), 2.11 (br d, J=10.9 Hz, 1H), 1.81-1.67 (m, 4H), 1.55-1.28 (m, 1H).

Step 4A: Preparation of (S)-4-(3-(but-2-ynamido)piperidin-1-yl)-5-fluoro-2,3-dimethyl-1H-indole-7-carboxamide

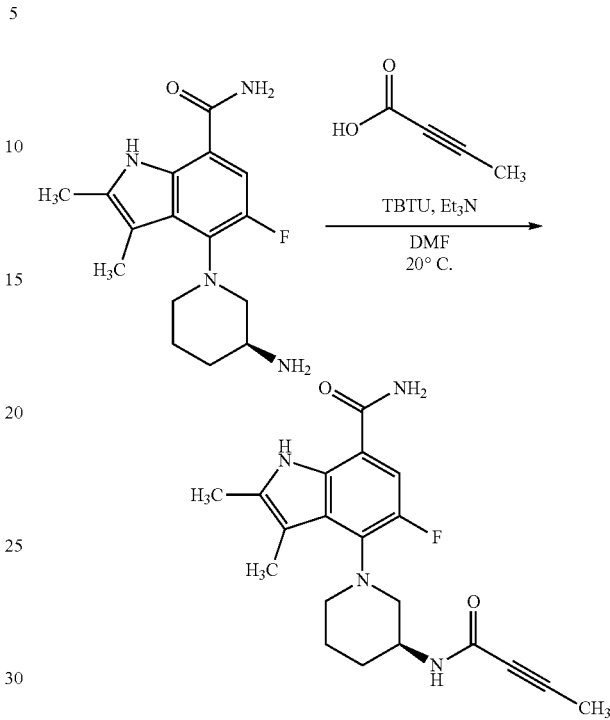

To Reactor-1 was charged N,N-dimethylformamide (DMF, 12.77 kg, 13.5 L). Reactor-1 was purged with $N_2$ to inert. (S)-4-(3-aminopiperidin-1-yl)-5-fluoro-2,3-dimethyl-1H-indole-7-carboxamide (3.0 kg, 1.0 equiv) was charged followed by 2-butynoic acid (0.854 kg, 1.04 equiv). Reactor-1 was rinsed with DMF (1.42 kg, 1.5 L). The mixture was sparged with $N_2$ for 20 min. Triethylamine (2.99 kg, 3.0 equiv) was charged followed by a DMF rinse (1.42 kg, 1.5 L). TBTU (0-(Benzotriazol-1-yl)-N,N,N',N'-tetramethyluronium tetrafluoroborate, 3.256 kg, 1.04 equiv) was charged followed by a DMF rinse (1.42 kg, 1.5 L). The reaction mixture was agitated for 1.5 h at 20° C. MeTHF (46.44 kg, 60 L) was charged to the batch. The reaction was quenched with LiCl (20 wt %, 26.76 kg, 24 L) at 20° C. The bottom aqueous layer was discharged as waste. The organic layer was washed with 2N HCl solution (24.48 kg, 24 L), 10 wt % sodium bicarbonate solution (25.44 kg, 24 L) and deionized water (24.0 kg, 24 L). THF (26.61 kg, 30 L) was charged into Reactor-1. The rich organic stream in MeTHF/THF was polish filtered. The stream was distilled down to 15 L at 75-100 Torr. Constant volume distillation was carried out at 15 L with THF feed (39.92 kg, 45 L). The stream was heated to 60° C. for 1 hr and cooled to 50° C. MTBE (33.30 kg, 45 L) was charged slowly over 2 h. The slurry was aged at 50° C. for 4 h and cooled to 20° C. over 2 h, and aged at 20° C. for >2 h. The 1$^{st}$ drop slurry was filtered and was rinsed with MTBE (8.88 kg, 12 L) twice. Wet cake was dried under vacuum 60 to 70° C. at 25 mbar overnight (>15 h). Reactor-1 was thoroughly cleaned with IPA. The dry cake was charged into Reactor-1 followed by the charge of IPA (47.10 kg, 60 L). The batch was heated to 60° C. to achieve full dissolution and cooled to 40° C. Rich organic (24 L) was transferred to Reactor-2 for crystallization. The stream was distilled at 24 L constant volume and 100 mbar using remaining rich organic from reactor-1 as distillation feed. Following distillation completion, the batch was heated to 60° C., aged at 60° C. for 2 h, cooled to 20° C. over 2 h, and aged at 20° C. over 2 h. The slurry was filtered. IPA (1.18 kg) was used to rinse the reactor and washed the cake. The wet cake was dried under vacuum at 70° C. and 25 mbar for >15 h. The dry cake (2.196 kg, 63.2% yield) was discharged as an off-white crystalline solid. $^1$H NMR (400 MHz, DMSO-$d_6$): δ 10.62 (s, 1H), 8.48 (d, J=7.1 Hz, 1H), 7.91 (s, 1H), 7.39 (d, J=7.4 Hz, 1H), 7.33 (s, 1H), 3.88 (m, 1H), 3.11 (t, J=8.0 Hz, 1H), 3.0 (m, 1H), 2.96 (m, 1H), 2.78 (t, J=10.0 Hz, 1H), 2.35 (s, 3H), 2.30 (s, 3H), 1.92 (s, 3H), 1.86 (m, 1H), 1.31 (m, 1H), 1.70 (m, 2H); $^{13}$C NMR (400 MHz, DMSO-$d_6$): δ 168.2, 153.2, 151.9, 134.4, 133.2, 132.1, 126.5, 112.3, 108.4, 106.0, 82.3, 75.7, 56.9, 51.9, 46.3, 29.7, 24.4, 11.1, 10.2, 3.0; LC-MS: M+H=371.2.

Step 4B: Alternative Preparation of (S)-4-(3-(but-2-ynamido)piperidin-1-yl)-5-fluoro-2,3-dimethyl-1H-indole-7-carboxamide

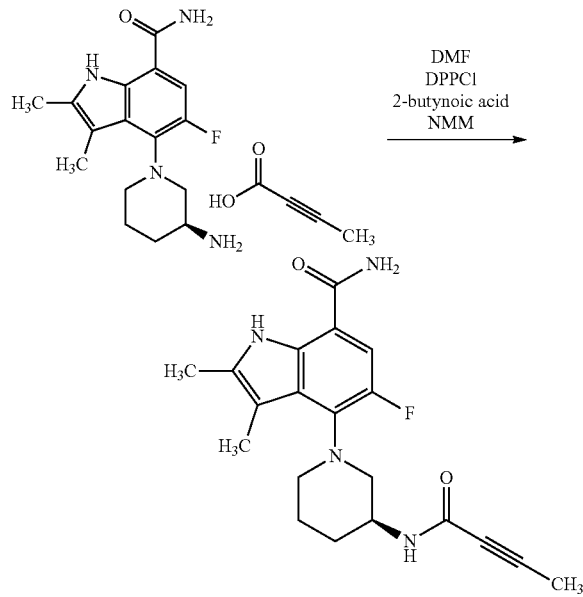

To Reactor-1 was charged N,N-dimethylformamide (DMF 4.5 mL, 4.5 mL/g). Reactor-1 was purged with $N_2$ to inert. (S)-4-(3-aminopiperidin-1-yl)-5-fluoro-2,3-dimethyl-1H-indole-7-carboxamide 2-butynoic acid salt (1.0 g, limiting reagent) was charged followed by 2-butynoic acid (0.065 g, 0.3 equiv.). The mixture was inerted with $N_2$ for 20 min. N-methylmorpholine (0.78 g, 3.0 equiv) was charged. Next, diphenylphosphinic chloride (0.79 g, 1.3 equiv) was charged over 0.5 h while maintaining the reaction temperature at 20-25° C. The reaction mixture was agitated for 1.5 hour at 20° C. Me-THF (14 mL, 14 mL/g) was charged to the reaction mixture. The reaction was quenched with the addition of aqueous NaCl (12.5 wt %, 6 mL, 6 mL/g) at 20° C. The bottom aqueous layer was discharged as waste. Aqueous NaCl (12.5 wt %, 6 mL, 6 mL/g) at 20° C. was added to the organic layer, stirred for 0.5 hour and the bottom aqueous layer was discharged to waste. Deionized water (6 mL, 6 mL/g) was charged to the organic layer, stirred for 0.5 hour and the bottom aqueous layer was discharged to waste. THF (8 mL, 8 mL/g) was charged into Reactor-1 and the mixture was concentrated under vacuum to remove Me-THF and water, and reconstituted in 4 L/kg of THF. The mixture was heated to 60° C. and stirred for 1 hour; the temperature was reduced to 50° C. and MTBE (12 mL, 12 mL/g) was added. The mixture was aged for 4 hours while maintaining the temperature of 50° C. and then cooled to room temperature. The solids were filtered and washed with MTBE (6.5 mL, 6.5 mL/g). The solids of crude were dried at 70° C. under vacuum for 12 hours.

Crude (S)-4-(3-(but-2-ynamido)piperidin-1-yl)-5-fluoro-2,3-dimethyl-1H-indole-7-carboxamide was charged to Reactor-2, followed by THF (12 mL, 12 mL/g). The mixture was stirred for 0.5 hour. The solution was polish filtered. The solution was concentrated under vacuum to remove THF and reconstituted in EtOH (7 mL, 7 mL/g). (S)-4-(3-(but-2-ynamido)piperidin-1-yl)-5-fluoro-2,3-dimethyl-1H-indole-7-carboxamide seeds (0.01 g, 0.01 g/g) were added, the mixture was heated to 60° C. and aged for 2 hours. n-heptane (21 mL, 21 mL/g) was added slowly over 4 hours. The mixture was aged for additional 2 hours at 60° C., followed by cooldown to room temperature. The slurry was filtered, washed with n-heptane (6 mL, 6 mL/g), and dried under vacuum at 70° C. for 12 hours. The dry cake (0.68 g, 71% yield) was discharged as an off-white crystalline solid. $^1$H NMR (400 MHz, DMSO-$d_6$): δ 10.62 (s, 1H), 8.48 (d, J=7.1 Hz, 1H), 7.91 (s, 1H), 7.39 (d, J=7.4 Hz, 1H), 7.33 (s, 1H), 3.88 (m, 1H), 3.11 (t, J=8.0 Hz, 1H), 3.0 (m, 1H), 2.96 (m, 1H), 2.78 (t, J=10.0 Hz, 1H), 2.35 (s, 3H), 2.30 (s, 3H), 1.92 (s, 3H), 1.86 (m, 1H), 1.31 (m, 1H), 1.70 (m, 2H); $^{13}$C NMR (400 MHz, DMSO-$d_6$): δ 168.2, 153.2, 151.9, 134.4, 133.2, 132.1, 126.5, 112.3, 108.4, 106.0, 82.3, 75.7, 56.9, 51.9, 46.3, 29.7, 24.4, 11.1, 10.2, 3.0; LC-MS: M+H=371.2.

Applicants have discovered a new synthesis process for the preparation of (S)-4-(3-(but-2-ynamido)piperidin-1-yl)-5-fluoro-2,3-dimethyl-1H-indole-7-carboxamide which offers significant advantages.

The new synthesis process utilizes fewer synthesis steps (4 vs 8) than the process disclosed in WO 2016/065226.

Additionally, the process of the present invention provided (S)-4-(3-(but-2-ynamido)piperidin-1-yl)-5-fluoro-2,3-dimethyl-1H-indole-7-carboxamide at an overall yield of 22% (step 1: 73.%, step 2: 69%, step 3: 69%, step 4: 63%). In comparison, (S)-4-(3-(but-2-ynamido)piperidin-1-yl)-5-fluoro-2,3-dimethyl-1H-indole-7-carboxamide was prepared according to the process of WO 2016/065226, which provided (S)-4-(3-(but-2-ynamido)piperidin-1-yl)-5-fluoro-2,3-dimethyl-1H-indole-7-carboxamide at an overall yield of 2.9% yield (step 1: 91%, step 2: 71%, step 3: 35%, step 4: 88%, step 5: 80%, step 6: 29%, step 7: 99%, step 8: 63%).

Furthermore, the process of the present invention does not include any transition metal-catalyzed steps, no genotoxic intermediates, and is adaptable to large scale manufacturing. In comparison, the process disclosed in WO 2016/065226 employed lead (Pb) in process step (8) and included a potentially genotoxic hydrazine intermediate in process step 8.

The process of the present invention has an estimated manufacturing cycle time of approximately 6 months versus a estimated manufacturing cycle time of approximately 12 months for the process disclosed in WO 2016/065226.

What is claimed is:

1. A process for preparing a compound of Formula (V):

(V) [Structure: indole-7-carboxamide with 2,3-dimethyl, 4-(3-aminopiperidin-1-yl), 5-fluoro substituents]

comprising the steps of:
(a) reacting a compound of Formula (I) and a compound of Formula (II):

(I) [Structure: benzoate with R₂R₁N, OR₃, F, X₁ substituents]

(II) [Structure: 3-(NR₄R₅)piperidine]

to provide a compound of Formula (III):

(III) [Structure: benzoate linked to piperidine]

and
(b) converting said compound of Formula (III) to said compound of Formula (V) by steps (b1), (b2), and (b3), in any order:
(b1) forming an indole group by reaction with a compound of Formula (IVa) or a compound of Formula (IVb):

(IVa) [Structure: CH₃C(O)CH(CH₃)X₂]

(IVb) [Structure: R₈O-CH(CH₃)-C≡CH]

(b2) converting said NR₄R₅ group to —NH₂; and
(b3) converting said —OR₃ group to —NH₂;

wherein:
$X_1$ is halo, —NO₂, —OS(O)₂R, or —N₂⁺;
$X_2$ is Cl, Br, I, —OH, —OS(O)₂R, acyloxy, or trialkylsiloxy;
$R_1$ and $R_2$ are independently selected from H, benzyl, substituted benzyl, 4-methoxyphenyl, acyl, —S(O)₂Ar, tert-butoxycarbonyl, or benzyloxycarbonyl;
$R_3$ is H, $C_{1-8}$ alkyl, aryl, or heteroaryl;
$R_4$ and $R_5$ are independently selected from H, benzyl, 4-methoxybenzyl, 4-methoxyphenyl, acyl, —S(O)₂R, tert-butoxycarbonyl, or benzyloxycarbonyl;
$R_8$ is H, $C_{1-3}$ alkyl, or aryl; and
each R is independently $C_{1-3}$ alkyl or aryl.

2. The process according to claim 1 wherein in Step (b), said compound of Formula (III) is converted to said compound of Formula (V) by:

reacting said compound of Formula (III) with said compound of Formula (IVa) or said compound of Formula (IVb) and converting said —NR₄R₅ group to —NH₂, either in a consecutive or concurrent order, or both, to provide a compound of Formula (Va)

(Va) [Structure: 2,3-dimethyl-2,3-dihydroindole-7-carboxylate with 4-(3-aminopiperidin-1-yl), 5-fluoro substituents]

and converting said —OR₃ group attached to said compound of Formula (Va) to —NH₂ to provide said compound of Formula (V).

3. The process according to claim 1 wherein in Step (b), said compound of Formula (III) is converted to said compound of Formula (V) by:

converting said —OR₃ group attached to said compound of Formula (III) to —NR₆R₇ to provide said compound of Formula (IIIa):

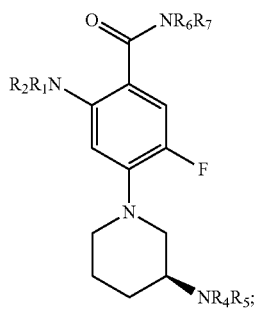

(IIIa)

reacting said compound of Formula (IIIa) with said compound of Formula (IVa) or said compound of Formula (IVb) to provide a compound of Formula (Vb):

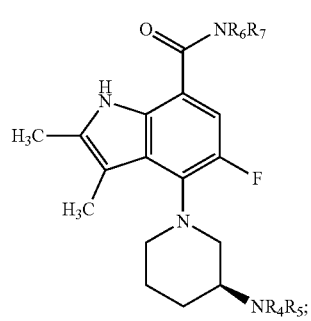

(Vb)

and converting each of said —NR₄R₅ group and said —NR₆R₇ group attached to the compound of Formula (Vb) to —NH₂, either in a consecutive or concurrent order, or both; wherein R₆ and R₇ are individually selected from H, benzyl, 4-methoxybenzyl 4-methoxyphenyl, allyl, acyl, formyl, —OH, —OR, tert-butoxycarbonyl, benzyloxycarbonyl or —S(O)₂R.

4. The process according to claim 1 wherein in Step (b1), said indole group is formed by reaction with said compound of Formula (IVa).

5. The process according to claim 1 wherein in Step (b1), said indole group is formed by reaction with said compound of Formula (IVb).

6. The process according to claim 1 further comprising the step of reacting the compound of Formula (V) with a compound of Formula (VI)

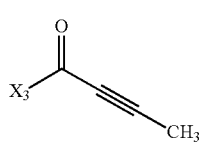

(VI)

to provide a compound of Formula (VII):

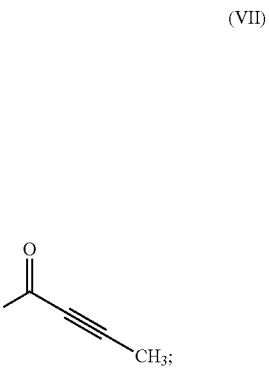

(VII)

wherein X₃ is —OH, halo, —OCH₃, —O(aryl), —OC(O)R, —OS(O)₂R, —OS(O)R, —OP(O)R₂, or —OP(O)(OR)₂.

7. A compound have the structure of Formula (Va):

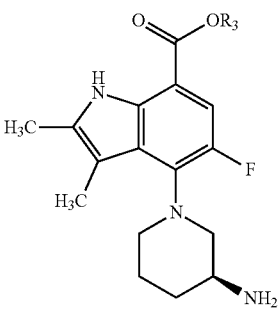

(Va)

or a salt thereof, wherein:
R₃ is C₁₋₆ alkyl unsubstituted or substituted with one or more R_a, benzyl unsubstituted or substituted with one or more R_a, or silyl; and
each R_a is independently F or Cl.

8. The compound according to claim 7 wherein R₃ is H or —CH₃.

9. The process according to claim 1 wherein:
X₁ is halo, —NO₂, —OS(O)₂R; and
R is C₁₋₃ alkyl.

10. The process according to claim 1 wherein:
X₂ is Cl, Br, I, —OH, —OS(O)₂R, acyloxy, or trialkylsiloxy; and
R is C₁₋₃ alkyl or aryl.

11. The process according to claim 1 wherein R₂ is H or benzyl.

12. The process according to claim 1 wherein R₃ is H or —CH₃.

13. The process according to claim 1 wherein:
R₄ is H; and
R₅ is benzyl, tert-butoxycarbonyl, or benzyloxycarbonyl.

14. The process according to claim 1 wherein:
R₁ is H;
R₂ is H;
R₃ is —CH₃;
R₄ is H;
R₅ is tert-butoxycarbonyl;
X₁ is F; and
X₂ is —OH.

15. The process according to claim 1 wherein step (a) is conducted in the presence of one or more synthesis adjuvants independently selected from organic bases, inorganic bases, nucleophilic catalysts, and transition metal catalysts.

16. The process according to claim 1 wherein step (a) is conducted at a reaction temperature in the range of from about 40° C. to about 140° C.

17. The process according to claim 1 wherein one or both of step (b1) and step (b2) are conducted in the presence of one or more synthesis adjuvants independently selected from diphenylphosphoric acid, dibenzylphosphoric acid, diphenylphosphinic acid, hydrochloric acid, hydrobromic acid, methanesulfonic acid, trifluoromethanesulfonic acid, trifluoroacetic acid, p-toluenesulfonic acid, benzenesulfonic acid, sulfuric acid, phosphoric acid, trichloroacetic acid, tin(II) chloride, tin(II) triflate, ytterbium triflate, aluminum triflate, bismuth triflate, zirconium chloride, titanium chloride, scandium triflate, and iron(III) triflate.

18. The process according to claim 1 wherein one or both of step (b1) and step (b2) are conducted at a temperature in the range of from about 40° C. to about 100° C.

19. The process according to claim 1 wherein step (b2) is conducted in the presence of one or more synthesis adjuvants independently selected from sodium formamide or 1,5,7-triazabicyclo[4.4.0]dec-5-ene.

20. The process according to claim 1 wherein step (b2) is conducted in a temperature in the range of from about 0° C. to about 100° C.

* * * * *

UNITED STATES PATENT AND TRADEMARK OFFICE
CERTIFICATE OF CORRECTION

PATENT NO. : 11,220,489 B2
APPLICATION NO. : 16/328447
DATED : November 1, 2022
INVENTOR(S) : Junying Fan et al.

Page 1 of 1

It is certified that error appears in the above-identified patent and that said Letters Patent is hereby corrected as shown below:

In the Claims

Claim 1, Column 36, Line 14, delete "NR$_4$R$_5$" and insert -- —NR$_4$R$_5$ --.

Claim 2, Column 36, Lines 42-56 (Approx.), delete

" 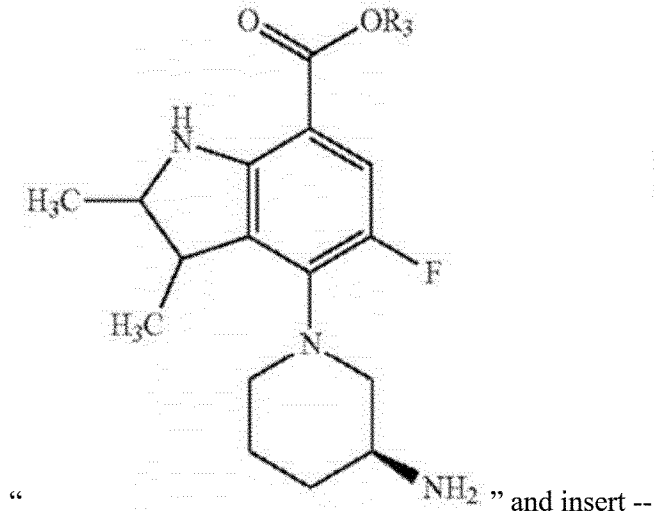 " and insert -- 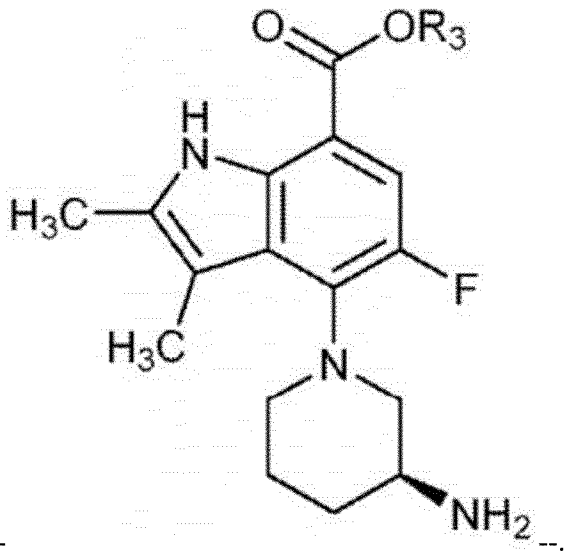 --.

Claim 3, Column 37, Line 42, after "4-methoxybenzyl" insert -- , --.

Signed and Sealed this
Sixteenth Day of September, 2025

Coke Morgan Stewart
*Acting Director of the United States Patent and Trademark Office*